US012692348B2

(12) United States Patent
Olsen et al.

(10) Patent No.: US 12,692,348 B2
(45) Date of Patent: Jul. 28, 2026

(54) SYNTHESIS OF NOVEL POLY(ESTER UREA)S FOR DRUG DELIVERY

(71) Applicant: Massachusetts Institute of Technology, Cambridge, MA (US)

(72) Inventors: Bradley D. Olsen, Arlington, MA (US); Hursh Vardhan Sureka, Cambridge, MA (US); Katharina Fransen, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 555 days.

(21) Appl. No.: 18/295,599

(22) Filed: Apr. 4, 2023

(65) Prior Publication Data

US 2023/0312827 A1 Oct. 5, 2023

Related U.S. Application Data

(60) Provisional application No. 63/326,925, filed on Apr. 4, 2022.

(51) Int. Cl.
*C08G 71/02* (2006.01)
*A61K 8/84* (2006.01)
*A61L 26/00* (2006.01)

(52) U.S. Cl.
CPC .............. *C08G 71/02* (2013.01); *A61L 26/00* (2013.01)

(58) Field of Classification Search
None
See application file for complete search history.

(56) References Cited

U.S. PATENT DOCUMENTS

| | | | | |
|---|---|---|---|---|
| 2007/0292476 | A1 | 12/2007 | Landis | |
| 2009/0029937 | A1* | 1/2009 | Chu | C12N 15/88 435/375 |
| 2012/0328706 | A1 | 12/2012 | Turnell | |
| 2016/0083731 | A1* | 3/2016 | Chu | A61K 31/7088 435/320.1 |
| 2017/0210852 | A1* | 7/2017 | Becker | C09J 175/02 |

FOREIGN PATENT DOCUMENTS

| | | | |
|---|---|---|---|
| CA | 2709412 | A1 * | 1/2009 |
| CA | 2048154 | A1 * | 11/2015 |

OTHER PUBLICATIONS

Diaz, et al., "New poly(ester urea) derived from l-leucine: Electrospun scaffolds loaded with antibacterial drugs and enzymes", Materials Science and Engineering, 46: 450 (2015).
ISR PCT/US2023/017410 mailed Jun. 22, 2023.

* cited by examiner

*Primary Examiner* — Tae H Yoon
(74) *Attorney, Agent, or Firm* — PABST PATENT GROUP LLP

(57) ABSTRACT

Disclosed are poly(ester urea)s containing two or more units containing two amino acid monomers linked by a linker. At least two units of the poly(ester urea)s are covalently bonded via a urea bond. Suitable amino acid monomers are lysine, arginine, aspartic acid, phenylalanine, or a side chain protected derivative thereof, and suitable linkers are selected from a 1,4-butane diol group, a 1,6-hexane diol group, diethylene glycol group, a triethylene glycol group, or an N-methyl diethanolamine group. The poly(ester urea)s are used to form polyplexes for the improved complexation and delivery of drugs to a subject in need thereof.

17 Claims, 14 Drawing Sheets

SYNTHESIS OF NOVEL POLY(ESTER UREA)S FOR DRUG DELIVERY

CROSS-REFERENCE TO RELATED APPLICATIONS

This application claims benefit of and priority to U.S. Ser. No. 63/326,925 filed Apr. 4, 2022, which is incorporated herein by reference in its entirety.

FIELD OF THE INVENTION

The invention is generally directed to polymeric materials for drug delivery, particularly poly(ester urea)s and methods of making and using thereof.

BACKGROUND OF THE INVENTION

Poly(ester urea)s (PEUs) have been demonstrated as effective materials for use in bone graft, adhesives, and surgical mesh amongst others because of their superior biocompatibility and biodegradability. Owing to these two properties of this class of material, PEUs make an interesting target for use in drug delivery. Polyelectrolyte complexation has been demonstrated as an effective method for the formation of nanoscale drug delivery particles including micelles, polyplexes, and thin-film coatings. However, in order to adapt PEUs to these applications, novel constitutive blocks, an amino acid and a diol, must be optimized for water solubility and complexation efficiency. This requires the use of novel amino acids and diols previously undemonstrated in literature.

Therefore, it is an object of the invention to provide improved compositions for drug delivery.

SUMMARY OF THE INVENTION

Disclosed are PEUs, polyplexes thereof, and their methods of use. The PEUs contain two or more units having a structure:

$[(AA1)_p\text{-linker-}(AA2)_q]$ or     Formula I $[(AA1)\text{-linker-}(AA2)]_n$     Formula II wherein:

n is an integer greater than 2, such as between 10 and 1000.

at least two units are covalently bonded via a urea bond;

each of AA1 and AA2 is independently an unprotected or protected amino acid monomer;

the linker is a linear or branched chemical moiety;

p and q are independently 1 or 2, and with the proviso that (i) when the linker consists of an aliphatic diol moiety and AA1 and AA2 are hydrophobic amino acid monomers, the aliphatic diol moiety consists of a $C_2$-$C_5$ aliphatic diol moiety or a $C_2$-$C_4$ aliphatic diol moiety; (ii) when the linker consists of a $C_6$-$C_{12}$ aliphatic diol moiety and AA1 and AA2 are hydrophobic amino acid monomers, the hydrophobic amino acid monomers do not contain a substituted aromatic side chain or unsubstituted aromatic side chain; (iii) when the linker consists of a $C_6$-$C_{12}$ aliphatic diol moiety and AA1 and AA2 are hydrophobic amino acid monomers, the hydrophobic amino acid monomers are not substituted phenyl alanine or unsubstituted phenyl alanine; (iv) when the linker consists of a branched chemical moiety, the amino acid monomer is not an unprotected aromatic amino acid monomer or a protected aromatic amino acid monomer; (v) when the linker consists of a $C(CH_3)(CH_2O—)_3$ moiety, the amino acid monomers are not an unprotected aromatic amino acid monomer or a protected aromatic amino acid monomer; and/or (vi) when the linker consists of a $C(CH_3)(CH_2O—)_3$ moiety, the amino acid monomers are not an unprotected tyrosine or a protected tyrosine.

In some forms the PEUs are as described above for Formula I and Formula II, except that the amino acid monomers contain a cationic amino acid monomer, an anionic amino acid monomer, an aromatic amino acid monomer, or a side chain protected derivative thereof. Preferably, the amino acid monomers are selected from lysine, arginine, aspartic acid, phenylalanine, or a side chain protected derivative thereof. Where an amino acid monomer contains a side chain protected derivative, a side chain of the amino acid contains a protecting moiety. In some forms, the protecting moiety in benzyloxycarbonyl or benzyl.

In some forms, the linker is formed from a 1,4-butane diol group, a 1,6-hexane diol group, diethylene glycol group, a triethylene glycol group, or an N-methyl diethanolamine group.

Preferably, the PEUs contain a structure selected from:

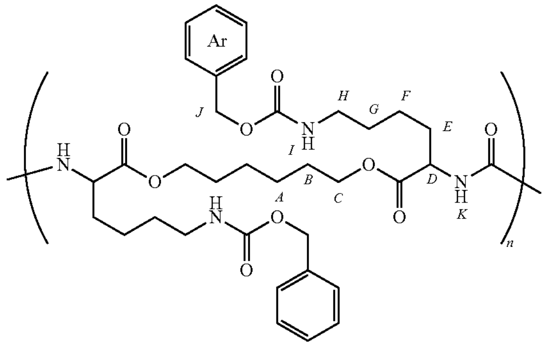

,

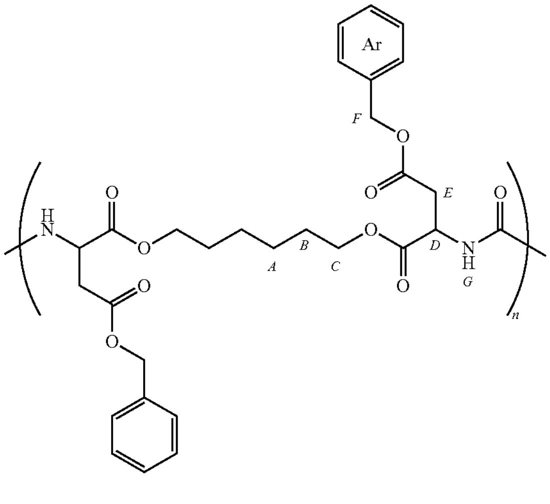

,

-continued

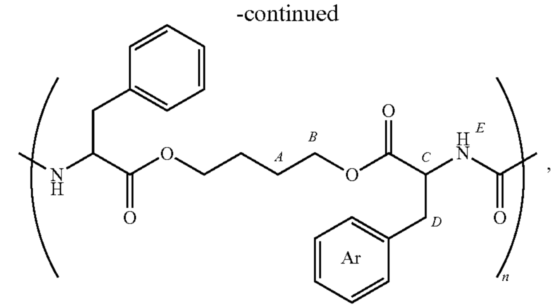

,

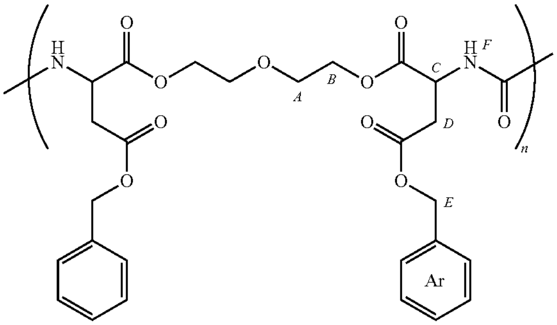

,

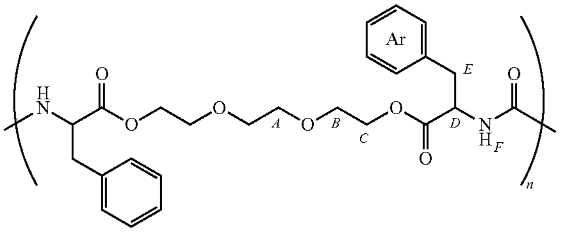

,

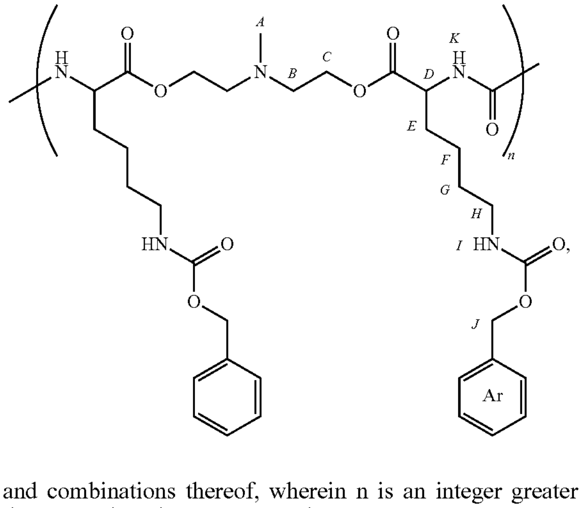

and combinations thereof, wherein n is an integer greater than 2, such as between 10 and 1000.

The PEUs can be used to form polyplexes for the improved complexation and delivery of one or more therapeutic, diagnostic, and/or prophylactic agents to a subject in need thereof. The polyplexes can be in the form of micelles, liquid polyplexes, or thin-film coatings. The polyplexes a contain a polyelectrolyte complex of a drug and the PEU disclosed herein. Therefore, in some forms, the micelle contains a polyelectrolyte complex of a drug and the PEU disclosed herein. In some forms, the liquid polyplex contains a polyelectrolyte complex of a drug and the PEU disclosed herein. In some forms, the thin-film coating contains a polyelectrolyte complex of a drug and the PEU disclosed herein.

The following Detailed Description references the accompanying drawings which form a part this application, and which show, by way of illustration, specific example implementations. Other implementations may be made without departing from the scope of the disclosure.

DETAILED DESCRIPTION OF THE INVENTION

I. Definitions

Figure 1:
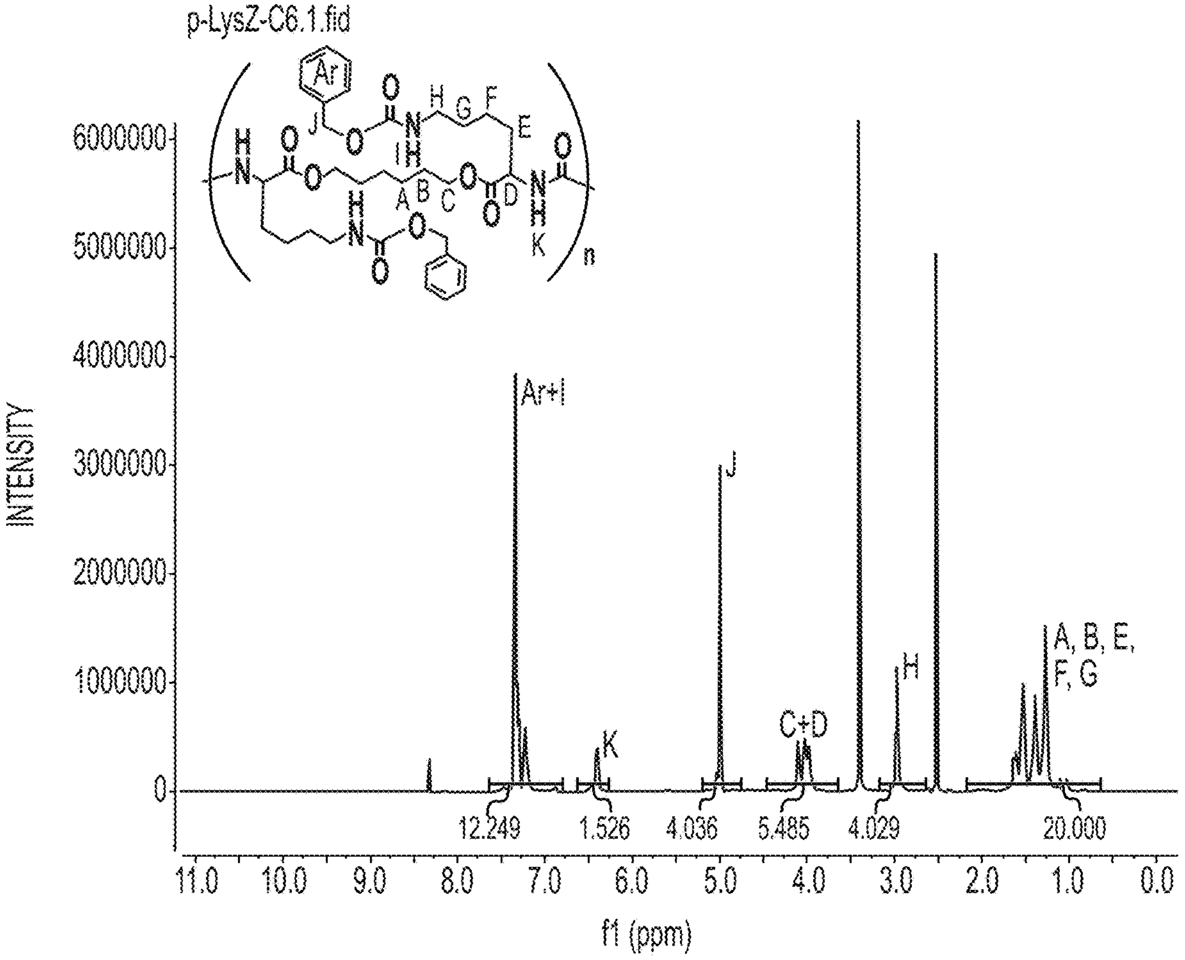
FIGS. 1-3 provide $^1$H NMR, and $^1$H-$^1$H COSY NMR of poly(1,6-hexanediol-l-lysine (CBZ))-based PEU (Lys(Z)-C6-PEU).

"About," as relates to numerical values described herein, refers to a value that is ±10% of the specified value. Specific values within this range are ±1%, ±2%, ±3%, ±4%, ±5%, ±6%, ±7%, ±8%, ±9%, and ±10%.

The term "amino acid" refers to a molecule containing both an amino group and a carboxyl group. Amino acids include alpha-amino acids and beta-amino acids. In certain forms, an amino acid is an alpha-amino acid. Amino acids can be natural or synthetic. Amino acids include, but are not limited to, the twenty standard or canonical amino acids: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). Common non-standard or non-canonical amino acids include, but are not limited to, selenocysteine, ornithine, pyrrolysine, and N-formylmethionine.

The term "natural amino acid" refers to both the D- and L-isomers of the 20 common naturally occurring amino acids found in peptides (e.g., A, R, N, C, D, Q, E, G, H, I, L, K, M, F, P, S, T, W, Y, V (as known by the one letter abbreviations)).

The terms "synthetic amino acid", "non-natural amino acid" and "unnatural amino acid," are used interchangeably, and refer to an organic compound that has an amino group and a carboxyl group, and is not one of the D- and L-isomers of the 20 common naturally occurring amino acids found in peptides. Generally, it mimics the reactivity of a natural amino acid due to the presence of the amino and carboxyl groups. "Synthetic amino acid," "non-natural amino acid," or "unnatural amino acid" also refers to an amino acid that is not produced by an organism without genetic engineering. The synthetic amino acid as defined herein generally increases or enhances the properties of a peptide (e.g., reactivity towards a desired molecule) when the synthetic amino acid is either substituted for a natural amino acid or incorporated into a peptide. "Synthetic amino acid," "non-natural amino acid," or "unnatural amino acid" can also refer to a natural amino acid whose side chain has been chemically modified to include a reactive group (e.g. alkyne; azide; alkene; triarylphosphine; aminooxy; carbonyl; hydrazide; sulfonyl chloride; maleimide; aziridine; —CN; acryloyl; acrylamide; sulfone; vinyl sulfone; cyanate; thiocyanate; isocyanate; isothiocyanate; alkoxysilane; dialkyl dialkoxysilane; diaryl dialkoxysilane; trialkyl monoalkoxysilane; vinyl silane; acetohydrazide; acyl azide; acyl halides; epoxide; glycidyl; carbodiimides; thiol; amine; phosphoramidate; vinyl ether; substituted hydrazine; an alkylene glycol bis(diester), e.g. ethylene glycol bis(succinate); thioester, e.g., alkyl thioester, α-thiophenylester, allyl thioester (e.g., allyl thioacetate, allyl thioproprionate); allyl ester (e.g., allyl acetate, allyl propionate); aryl acetate (e.g. phenacyl ester); orthoester; sulfonamide, e.g. 2-N-acyl nitrobenzenesulfonamide; vinyl sulfide; or a combination thereof) such that the resulting amino acid is structurally different from any of the 20 canonical naturally occurring amino acids.

"Anionic amino acid" refers to an amino acid that as a net negative charge at neutral pH. Non-limiting examples include aspartic acid and glutamic acid.

"Aromatic amino acid" refers to an amino acid that has an aromatic group in its side chain. Non-limiting examples include phenylalanine, tyrosine, tryptophan, and histidine.

"Cationic amino acid" refers to an amino acid that has a net positive charge at neutral pH. Non-limiting examples include lysine, arginine, and ornithine.

"Chemical moiety" refers to a part of a molecule, such as an organic molecule.

"Pharmaceutically acceptable," refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration. A "pharmaceutically acceptable carrier," refers to all components of a pharmaceutical formulation which facilitate the delivery of the composition in vivo. Pharmaceutically acceptable carriers include, but are not limited to, diluents, preservatives, binders, lubricants, disintegrators, swelling agents, fillers, stabilizers, and combinations thereof.

The term "polyplex," as used herein, refers to a composition that contains a poly(ester urea) in complex with one or more therapeutic, prophylactic, or diagnostic agents. An example includes a complex between a poly(ester urea) and a polymeric therapeutic, prophylactic, or diagnostic agent. Thus, a polyplex can be in the form of micelles, nanoparticles, microparticles, films (e.g., thin films). The interaction between the poly(ester urea) and the one or more therapeutic, prophylactic, or diagnostic agents includes non-covalent interactions such as electrostatic interactions, hydrogen bonding interactions, metal coordination, physical adsorption, host-guest interactions, hydrophobic interactions, π-stacking interactions, van der Waals interactions, and dipole-dipole interactions.

"Side chain protected derivative thereof," as relates to an amino acid monomer in the instant poly(ester urea)s, refers to an amino acid whose chain contains an amino acid protecting group moiety. Non-limiting examples of protecting group moieties include benzyloxycarbonyl and benzyl.

"Small molecule" generally refers to an organic molecule that is less than about 2500 Da, such as between 100 Da and 2500 Da. Typically, small molecules are non-polymeric and/or non-oligomeric.

II. Compositions

Described are PEUs and polyplexes thereof. The PEUs are designed for improved water solubility and complexation efficiency. In some forms, an anionic amino acid and a cationic amino acid, such as aspartic acid and lysine, respectively, were incorporated into PEUs, as well as four diols with increased water solubility, butanediol (C4), diethylene glycol (DEG), triethylene glycol (TEG), and methyl diethanolamine (MDEA). Together the addition of these new functionalities allows for a vast array of PEUs with varying solubility, mechanical, and complexation properties to be synthesized enabling fine tuning of this class of materials for drug delivery and other applications. For example, the PEUs can be used for polyelectrolyte complexation with drugs for the delivery of these drugs. The PEUs can be used to form polyplexes. The polyplexes can be in the form of micelles, liquid polyplexes, or thin-film coatings.

A. Poly(Ester Urea)s

The PEUs contain two or more units having a structure:

$$[(AA1)_p\text{-linker-}(AA2)_q] \qquad \text{Formula I}$$

wherein:

at least two units are covalently bonded via a urea bond;

each of AA1 and AA2 is independently an unprotected or protected amino acid monomer;

the linker is a linear or branched chemical moiety;

p and q are independently 1 or 2, and with the proviso that (i) when the linker consists of an aliphatic diol moiety and AA1 and AA2 are hydrophobic amino acid monomers, the aliphatic diol moiety consists of a $C_2$-$C_5$ aliphatic diol moiety or a $C_2$-$C_4$ aliphatic diol moiety; (ii) when the linker consists of a $C_6$-$C_{12}$ aliphatic diol moiety and AA1 and AA2 are hydrophobic amino acid monomers, the hydrophobic amino acid monomers do not contain a substituted aromatic side chain or unsubstituted aromatic side chain; (iii) when the linker consists of a $C_6$-$C_{12}$ aliphatic diol moiety and AA1 and AA2 are hydrophobic amino acid monomers, the hydrophobic amino acid monomers are not substituted phenyl alanine or unsubstituted phenyl alanine; (iv) when the linker consists of a branched chemical moiety, the amino acid monomer is not an unprotected aromatic amino acid monomer or a protected aromatic amino acid monomer; (v) when the linker consists of a $C(CH_3)(CH_2O—)_3$ moiety, the amino acid monomers are not an unprotected aromatic amino acid monomer or a protected aromatic amino acid monomer; (vi) when the linker consists of a $C(CH_3)(CH_2O—)_3$ moiety, the amino acid monomers are not an unprotected tyrosine or a protected tyrosine, and/or (vii) the amino acid monomer is not a valine, leucine, iso-leucine, or serine when the linker is a 1,12-dodecane diol. As described herein, combinations of these provisos can be selected from options (i), (ii), (iii), (iv), (v), (vi), and (vii) and these are expressly disclosed.

In some forms, the PEUs are as described above, expected that they contain a structure:

$$[(AA1)\text{-linker-}(AA2)]_n \qquad \text{Formula II}$$

wherein n is an integer greater than 2, such as between 10 and 1000.

In some forms the PEUs are as described above for Formula I and Formula II, except that the amino acid monomers contain a cationic amino acid monomer, an anionic amino acid monomer, an aromatic amino acid monomer, or a side chain protected derivative thereof. In some forms the PEUs are as described above for Formula I and Formula II, except that the amino acid monomers contain a cationic amino acid monomer, an anionic amino acid monomer, or a side chain protected derivative thereof. In some forms the PEUs are as described above for Formula I and Formula II, except that the amino acid monomers contain a cationic amino acid monomer or a side chain protected derivative thereof. In some forms the PEUs are as described above for Formula I and Formula II, except that the amino acid monomers an anionic amino acid monomer or a side chain protected derivative thereof. In some forms the PEUs are as described above for Formula I and Formula II, except that the amino acid monomers contain an aromatic amino acid monomer or a side chain protected derivative thereof. Preferably, the amino acid monomers are selected from lysine, arginine, ornithine, histidine, aspartic acid, glutamic acid, phenylalanine, tyrosine, or a side chain protected derivative thereof.

Where an amino acid monomer contains a side chain protected derivative, a side chain of the amino acid contains a protecting moiety. In these forms, protecting moieties include, but are not limited to, benzyloxycarbonyl, benzyl, allyloxycarbonyl, 9-fluorenylmethoxycarbonyl, tert-butyloxycarbonyl, tert-butyl, trityl, 2,4-dimethoxybenzyl, 9-fluorenylmethyl, 2,2,4,6,7-pentamethyl-2,3-dihydrobenzofuran-5-sulfonyl, 9-xanthenyl, tosyl, benzyloxymethyl, formyl, tert-butyldimethylsilyl, allyl, o-nitrobenzyl, acetamidomethyl, etc. In some forms, the protecting moiety in benzyloxycarbonyl or benzyl.

In some forms, the PEUs are as described above for Formula I and Formula II, except that the PEUs have a structure:

Formula III

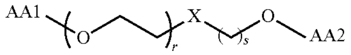

wherein:

X is absent or —NR—, wherein R is hydrogen, unsubstituted alkyl, or substituted alkyl;

r is an integer from 1 to 10, or 1 to 5, such as 1, 2, 3, 4, 5, 6, 7, 8, 9, or 10, s is an integer from 0 to 10, or 0 to 5, such as 0, 1, 2, 3, 4, 5, 6, 7, 8, 9, or 10.

In some forms, the PEUs are as described above for Formula III, except that:

(i) r is 1, x is absent, and s is 2 (i.e., the linker is formed from a 1,4-butane diol group);

(ii) r is 1, x is absent, and s is 4 (i.e., the linker is formed from a 1,6-hexane diol group);

(iii) r is 2, x is absent and s is 0 (i.e., the linker is formed from a diethylene glycol group);

(iv) r is 3, x is absent and s is 0 (i.e., the linker is formed from a triethylene glycol group); or (v) r is 1, x is —NR—, and s is 2 (i.e., the linker is formed from an N-methyl diethanolamine group).

In some forms, the PEUs are as described above for Formula I, Formula II, and Formula III, except that the PEUs are selected from:

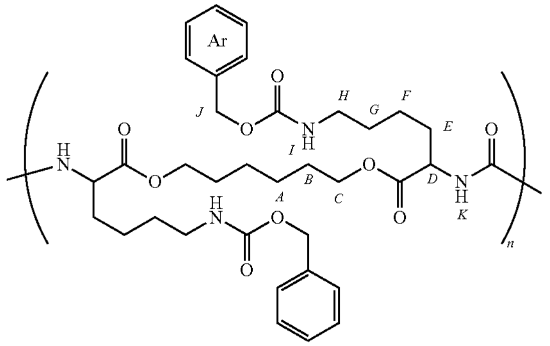
,

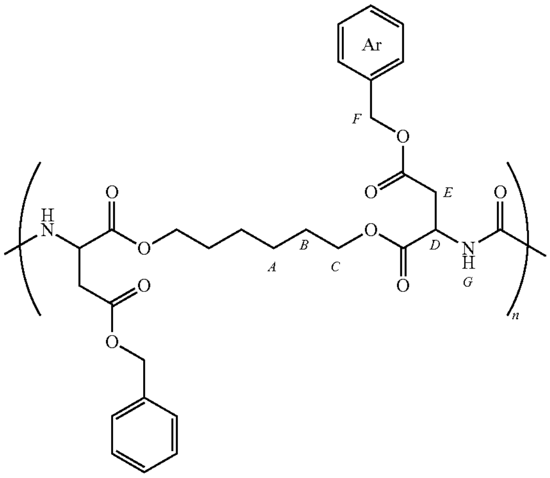
,

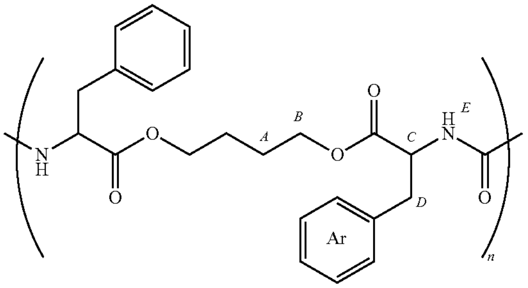
,

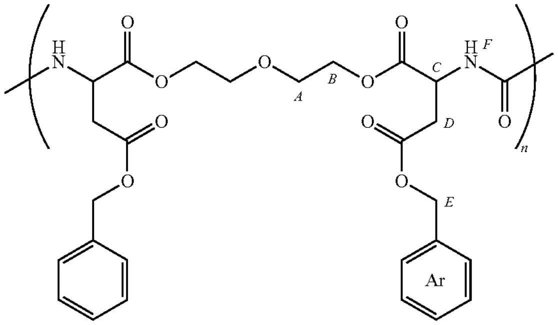
,

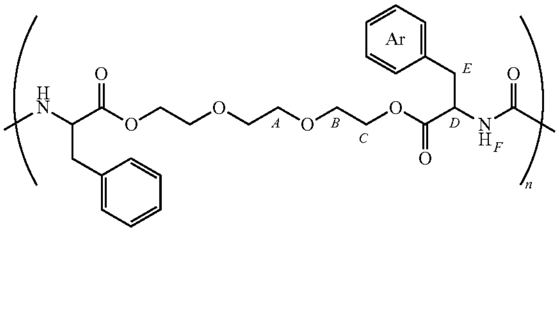
,

-continued
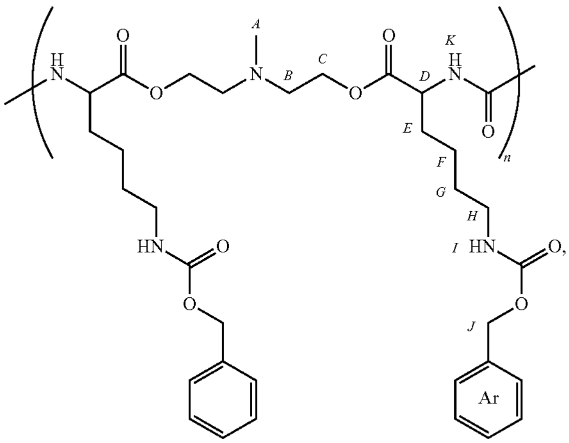
and combinations thereof.
In some forms, the PEUs are as described above for Formula I, except that the linker is a branched chemical moiety constituting a structure selected from:
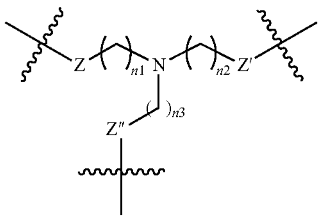
,
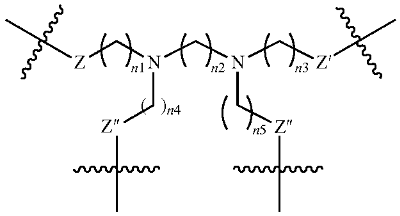
,
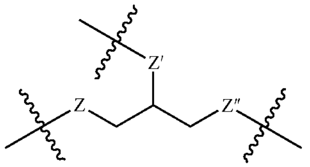
,
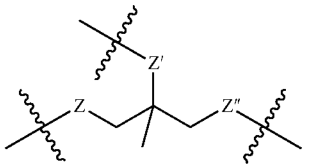
,
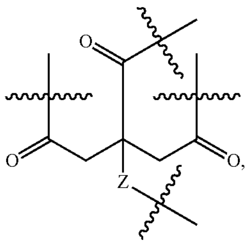
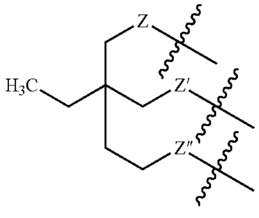
,
-continued
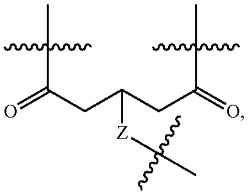
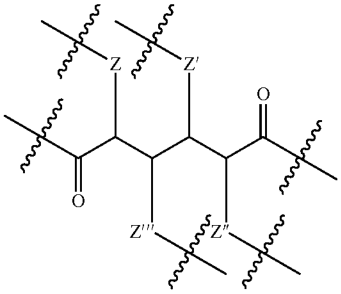
,
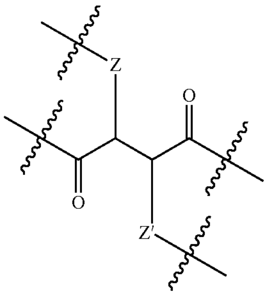
,
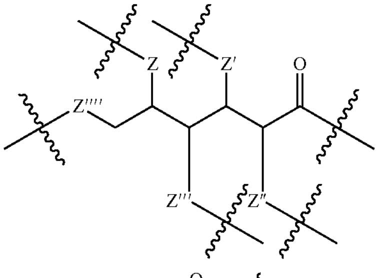
,
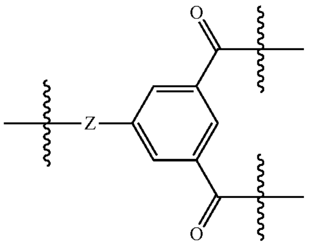
,
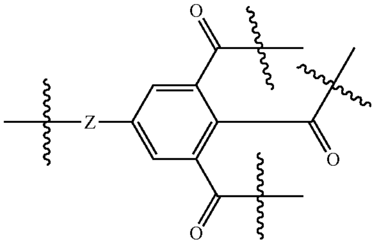
, -continued

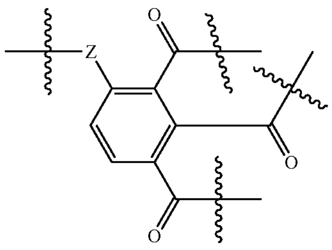

, and a combination thereof, wherein each Z, Z', Z'', Z''', and Z'''' is independently O, S, or NRy, wherein Ry is hydrogen, substituted or unsubstituted alkyl, substituted or unsubstituted aryl, and each n1, n2, n3, n4, and n5 is independently an integer between 1 and 20, between 1 and 15, between 1 and 10, between 1 and 5, such as 1, 2, 3, 4, 5, 6, 7, 8, 9, 10, 11, 12, 13, 14, 15, 16, 17, 18, 19, and 20; preferably, Ry is hydrogen, substituted or unsubstituted alkyl.

In some forms, the PEUs are as described above for Formula I, except that the linker is a branched chemical moiety constituting a structure selected from:

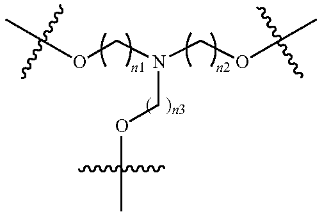

,

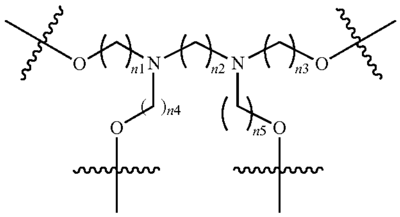

,

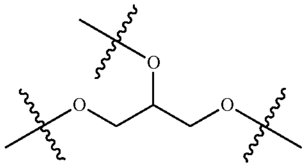

,

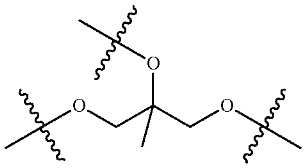

,

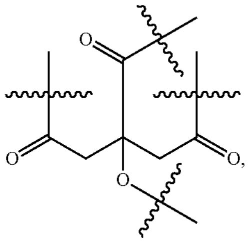

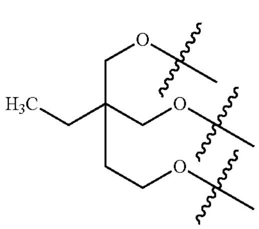

,

-continued

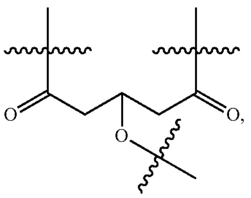

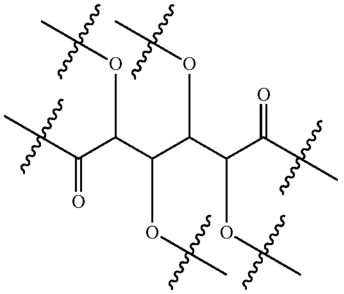

,

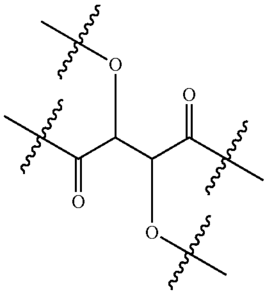

,

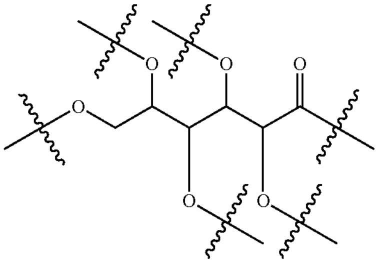

,

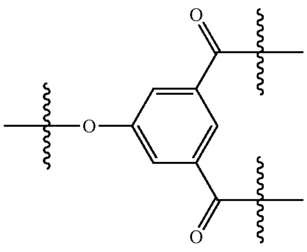

,

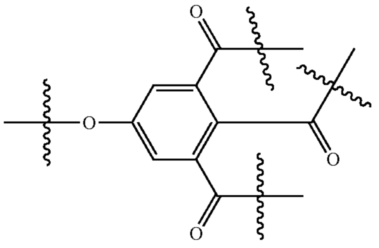

,

-continued

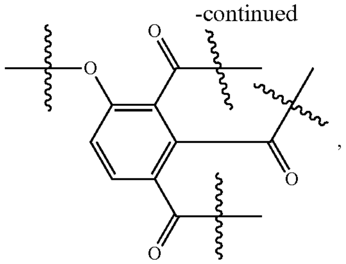

and a combination thereof, wherein n1, n2, n3, n4, and n5 are 2.

In general, and with respect to the PEUs described herein, the values of p, q, and n are such that the weight average molecular weights of the PEUs are between 1 kDa than 1 MDa, between 1 kDa and 750 kDa, between 1 kDa and 500 kDa, between 1 kDa and 100 kDa, between 1 kDa and 75 kDa, or between 1 kDa and 50 kDa.

B. Polyplexes

Also described are polyplexes containing the PEUs described herein in complex with one or more one or more therapeutic, prophylactic, or diagnostic agents. The polyplexes can be in the form of micelles, liquid polyplexes, or a thin-film coating.

The size of the micelles can vary. In some forms the micelles can be microparticles having a diameter of at least 1 μm and less than 1000 μm. In some forms, the micelles can nanoparticles having a diameter greater than 1 nm and less than 1000 nm.

The thin-film coating can be single-layered, multi-layered, unidirectional (i.e., release drug through only one side), multi-directional (i.e., release drug through at least two sides), or a combination thereof.

C. Agents to be Delivered

The polyplexes can be used for carrying, presenting, and/or delivering therapeutic agents, diagnostic agents, and/or prophylactic agents. Preferably, these agents are non-covalently conjugated to PEUs in the polyplexes. Each of these agents can be associated with the surface of the polyplexes, encapsulated within the polyplex, and/or dispersed throughout a matrix of PEUs of the polyplexes.

In some forms, the agents can be, independently, nucleic acids, proteins, peptides, lipids, polysaccharides, small molecules, or a combination thereof.

Pharmaceutical compositions containing the polyplexes can be formulated for entera or parenteral administration. The compositions are designed according to the route of administration and can be formulated in dosage forms appropriate for each route of administration. The polyplexes and pharmaceutical compositions can be administered by injection or transplantation. If fabricated for oral delivery, the pharmaceutical compositions can be delivered in an enteric capsule.

The pharmaceutical compositions can be in the form of a suspension or emulsion. In general, pharmaceutical compositions are provided including effective amounts of the therapeutic, diagnostic, and/or prophylactic agents and optionally include pharmaceutically acceptable diluents, preservatives, solubilizers, emulsifiers, and/or carriers. Such compositions include sterile water, buffered saline of various buffer content (such as, Tris HCl, acetate, phosphate), pH and ionic strength; and optionally, additives such as detergents and solubilizing agents (such as, TWEEN® 20, TWEEN® 80 also referred to as polysorbate 20 or 80), anti-oxidants (such as, ascorbic acid, sodium metabisulfite), and preservatives. Preferably, the suspension or emulsion include water, physiologically acceptable aqueous solutions containing salts and/or buffers, such as phosphate buffered saline (PBS), or any other aqueous solution acceptable for administration to an animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate. Examples of non-aqueous solvents or vehicles are propylene glycol, polyethylene glycol, vegetable oils, such as olive oil and corn oil, gelatin, and injectable organic esters such as ethyl oleate.

Carriers for pulmonary formulations can be divided into those for dry powder formulations and for administration as emulsion or suspension. Aerosols for the delivery of therapeutic agents to the respiratory tract are known in the art. For administration via the upper respiratory tract, the formulation can be formulated into an emulsion or a suspension containing an aqueous component, such as, water or isotonic saline, buffered or un-buffered, or as a suspension, for intranasal administration as drops or as a spray. The term aerosol as used herein refers to any preparation of a fine mist of particles, which can be in emulsion or a suspension, whether or not it is produced using a propellant. Aerosols can be produced using standard techniques, such as ultrasonication or high-pressure treatment. One skilled in the art can readily determine a suitable saline content and pH for an innocuous emulsion or a suspension for nasal and/or upper respiratory administration.

The formulations may be lyophilized and redissolved or resuspended immediately before use. The formulation may be sterilized by, for example, filtration through a bacteria retaining filter, by incorporating sterilizing agents into the compositions, by irradiating the compositions, or by heating the compositions.

Every polymer within the above definition of Formula I and Formula II is intended to be and should be considered to be specifically disclosed herein. Further, every subgroup that can be identified within the above definition is intended to be and should be considered to be specifically disclosed herein. As a result, it is specifically contemplated that any polymer or subgroup of polymers can be either specifically included for or excluded from use or included in or excluded from a list of polymers. For example, any one or more of the polymers described herein, with a structure depicted herein, or referred to in the Figures or the Examples herein can be specifically included, excluded, or combined in any combination, in a set or subgroup of such polymer. Such specific sets, subgroups, inclusions, and exclusions can be applied to any aspect of the compositions and methods described here. For example, a set of polymers that specifically excludes one or more particular polymers can be used or applied in the context of polymers per se (for example, a list or set of polymers), compositions including the polymers (including, for example, pharmaceutical compositions), any one or more of the disclosed methods, or combinations of these. Different sets and subgroups of polymers with such specific inclusions and exclusions can be used or applied in the context of polymers per se, compositions including one or more of the polymers, or any of the disclosed methods. All of these different sets and subgroups of polymers—and the different sets of polymers, compositions, and methods using or applying the polymers—are specifically and individual contemplated and should be considered as specifically and individually described. As an example, any of the groups of chemical moieties or substituents, as defined above, can be specifically included or excluded, as a group or individually, from any position in the polymers per se (for example, a list or set of polymers), from polymers in compositions (including, for example, pharmaceutical compositions), or any one or more of the disclosed methods, or combinations of these. For instance, in some forms, the amino acid monomer is not a valine, leucine, iso-leucine, or serine. In some forms, the amino acid monomer is not a valine, leucine, iso-leucine, or serine when the linker is a 1,12-dodecane diol, given that these do not contain a charged side chain for forming polyelectrolyte complexes.

III. Methods of Making and Reagents therefor

Methods of making the particles and components thereof are also provided.

The poly(ester urea)s were synthesized by generally reacting an amino acid and a bifunctional compound (e.g., a diol) in an appropriate organic solvent such as toluene in the presence of p-toluene sulfonic acid, and polymerizing the product in the presence of trisphosgene.

The polyplexes described herein can be formed using a variety of techniques known in the art. The technique to be used can depend on a variety of factors including the PEUs used to form the polyplexes, the desired size range of the resulting polyplexes, and suitability for the therapeutic, diagnostic, and/or prophylactic agent to be incorporated. Suitable techniques include, but are not limited to:

A. Solvent Evaporation

In this method the polymer is dissolved in a volatile organic solvent. The therapeutic, diagnostic, and/or prophylactic agents (either soluble or dispersed as fine particles) is added to the solution, and the mixture is suspended in an aqueous solution that contains a surface active agent such as poly(vinyl alcohol). The resulting emulsion is stirred until most of the organic solvent evaporated, leaving solid nanoparticles. The resulting nanoparticles are washed with water and dried overnight in a lyophilizer. Nanoparticles with different sizes and morphologies can be obtained by this method.

B. Solvent Removal

In this method, the therapeutic, prophylactic, and/or diagnostic agent is dispersed or dissolved in a solution of the selected polymer in a volatile organic solvent. This mixture is suspended by stirring in an organic oil (such as silicon oil) to form an emulsion. Unlike solvent evaporation, this method can be used to make: nanoparticles from polymers with high melting points and different molecular weights. The external morphology of spheres produced with this technique is highly dependent on the type of polymer used.

C. Spray-Drying

In this method, the polymer is dissolved in organic solvent. A known amount of the therapeutic, prophylactic, and/or diagnostic agent is suspended (insoluble drugs) or co-dissolved (soluble drugs) in the polymer solution. The solution or the dispersion is then spray-dried.

D. Phase Inversion

Nanospheres can be formed from polymers using a phase inversion method wherein a polymer is dissolved in a “good” solvent, fine particles of a substance to be incorporated, such as the therapeutic, prophylactic, and/or diagnostic agent, are mixed or dissolved in the polymer solution, and the mixture is poured into a strong non solvent for the polymer, to spontaneously produce, under favorable conditions, polymeric microspheres, wherein the polymer is either coated with the particles or the particles are dispersed in the polymer. The method can be used to produce nanoparticles in a wide range of sizes, including, for example, about 100 nanometers to about 10 microns. Substances which can be incorporated include, for example, imaging agents such as fluorescent dyes, or biologically active molecules such as proteins or nucleic acids. In the process, the polymer is dissolved in an organic solvent and then contacted with a non-solvent, which causes phase inversion of the dissolved polymer to form small spherical particles, with a narrow size distribution optionally incorporating an antigen or other substance.

E. Microfluidics

In general, a microfluidic device contains at least two channels that converge into a mixing apparatus. The channels are typically formed by lithography, etching, embossing, or molding of a polymeric surface. A source of fluid is attached to each channel, and the application of pressure to the source causes the flow of the fluid in the channel. The pressure may be applied by a syringe, a pump, and/or gravity. The inlet streams of solutions with polymers (such as poly(ester urea)s), therapeutic, prophylactic, and/or diagnostic agent, etc. converge and mix, and the resulting mixture is combined with a polymer non-solvent solution to form the particles having the desired size and/or density of moieties on the surface. By varying the pressure and flow rate in the inlet channels and the nature and composition of the fluid sources nanoparticles can be produced having reproducible size and structure.

F. Nanoprecipitation

In some forms, the polyplexes can be prepared via the nanoprecipitation approach. In this method, water-soluble or water-miscible organic solvents are used to dissolve the polymer and form emulsion upon mixing with the aqueous phase preferably under moderate stirring. The quick diffusion of the organic solvent into water leads to the formation of nanoparticles immediately after the mixing. After formation of nanoparticles, the solvents can be removed under low/reduced pressure. Nanoprecipitation can be used to encapsulate hydrophobic or hydrophilic therapeutic, prophylactic, and/or diagnostic agent, although the method is typically used to encapsulate hydrophobic compounds.

Thin film coatings can be formed using mechanical processes that involve compressing a composition containing the PEUs at room temperature and at elevated suitable pressures above atmospheric pressure.

IV. Methods of Using

The PEUs described herein have a wide range of applications, material choices, and application locations, for delivery of therapeutic agents, diagnostic agents, and/or prophylactic agents. The PEUs can be particularly useful in the controlled release of these agents.

The methods of treatment typically include using polyplexes loaded with one or more active agents, to deliver the one or more active agents into cells, or to a cell's microenvironment. The methods typically include contacting the active agent-loaded polyplexes with one more cells. The contacting can occur in vivo or in vitro or ex vivo.

Administration of a drug or other cargo to cells or a subject using polyplexes can be compared to a control, for example, delivery of the drug or other cargo to cells or a subject using conventional delivery methods such as free cargo/drug delivery. In some embodiments toxicity is reduced or absent compared to conventional delivery methods.

A. In Vivo Methods

The disclosed compositions can be used in a method of delivering active agents to cells in vivo. In some in vivo approaches, the compositions are administered to a subject in a therapeutically effective amount. As used herein, the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

The disclosed compositions can be for cell transfection of polynucleotides. The transfection can occur in vitro or in vivo, and can be applied in applications including gene therapy and disease treatment. The compositions can be more efficient, less toxic, or a combination thereof when compared to a control. The polynucleotides can be composed RNA, DNA, synthetic or modified nucleic acids, or a combination thereof.

B. In Vitro and Ex Vivo Methods

The disclosed compositions can be used in a method of delivering active agents to cells in vitro and ex vivo. For example, the polyplexes can be used for in vitro or ex vivo drug delivery to, or transfection of, cells. The method typically involves contacting the cells with particles including an active agent in an effective amount to introduce the active agent into the cell's cytoplasm. In some embodiments, the polynucleotide or drug is delivered to the cells in an effective amount to change the genotype or a phenotype of the cell. The cells can be primary cells isolated from a subject, or cells of an established cell line. The cells can be of a homogenous cell type, or can be a heterogeneous mixture of different cell types. The cells can be part of a tissue or organ.

Any eukaryotic cell or cells can be the target cell or cells. Suitable types of cells include, but are not limited to, undifferentiated or partially differentiated cells including stem cells, totipotent cells, pluripotent cells, embryonic stem cells, inner mass cells, adult stem cells, bone marrow cells, cells from umbilical cord blood, and cells derived from ectoderm, mesoderm, or endoderm. Suitable differentiated cells include somatic cells, neuronal cells, skeletal muscle, smooth muscle, pancreatic cells, liver cells, and cardiac cells.

In vitro or ex vivo treated cells, tissue, organs, etc. can be administered to subject in need thereof in a therapeutically effective amount. For example, target cells can be first isolated from a donor using methods known in the art, contacted with the polyplexes including a drug or polynucleotide. The treated cells can then be administered to a patient in need thereof. Sources or cells include cells harvested directly from the patient or an allographic donor. In preferred embodiments, the target cells to be administered to a subject will be autologous, e.g., derived from the subject, or syngeneic. Allogeneic cells can also be isolated from antigenically matched, genetically unrelated donors (identified through a national registry), or by using target cells obtained or derived from a genetically related sibling or parent.

Those skilled in the art will recognize, or be able to ascertain using no more than routine experimentation, many equivalents to the specific embodiments of the invention described herein. Such equivalents are intended to be encompassed by the following claims.

EXAMPLES

Example 1: Synthesis of poly(ester urea)s

Figure 2:
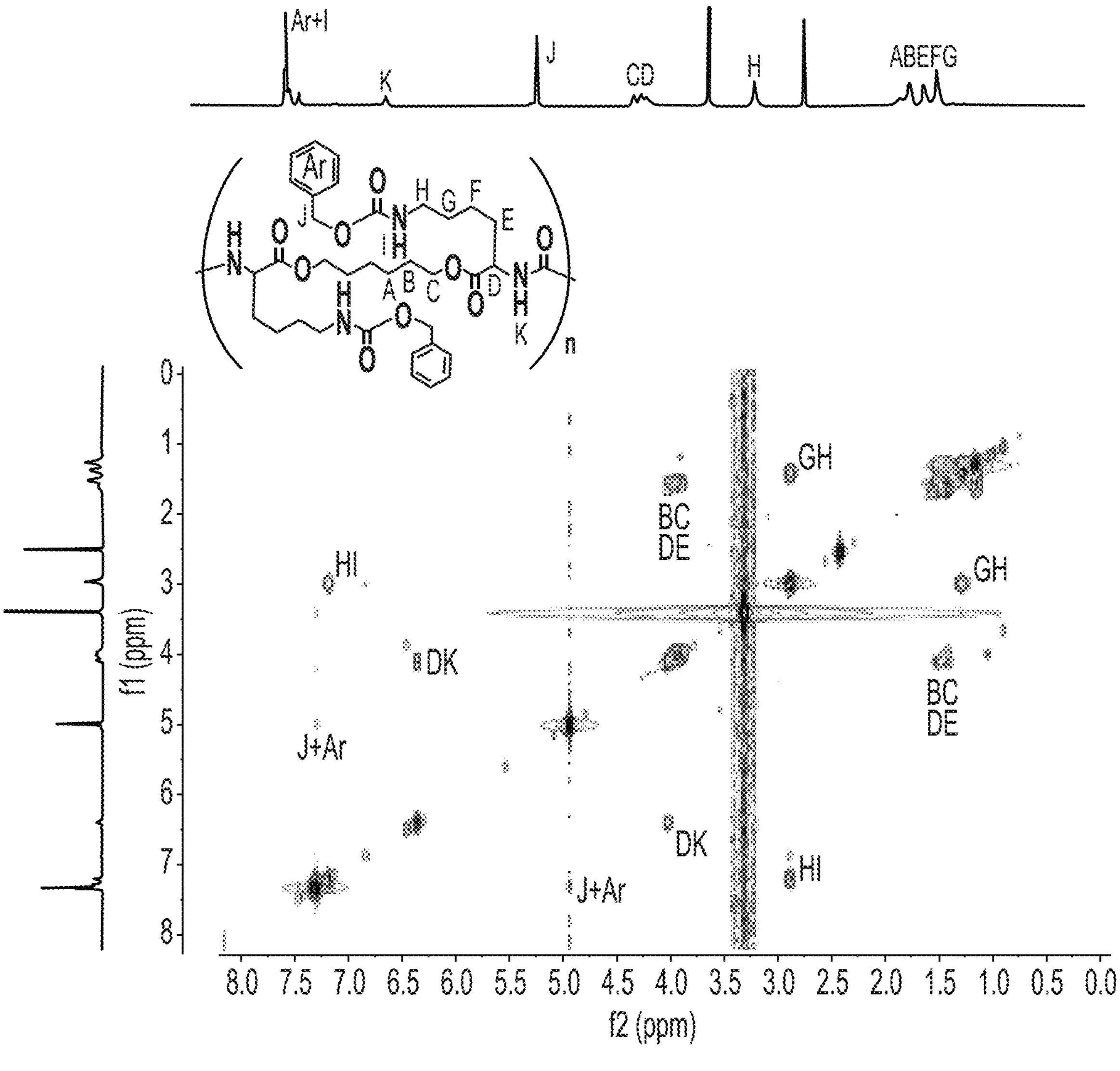
Figure 3:
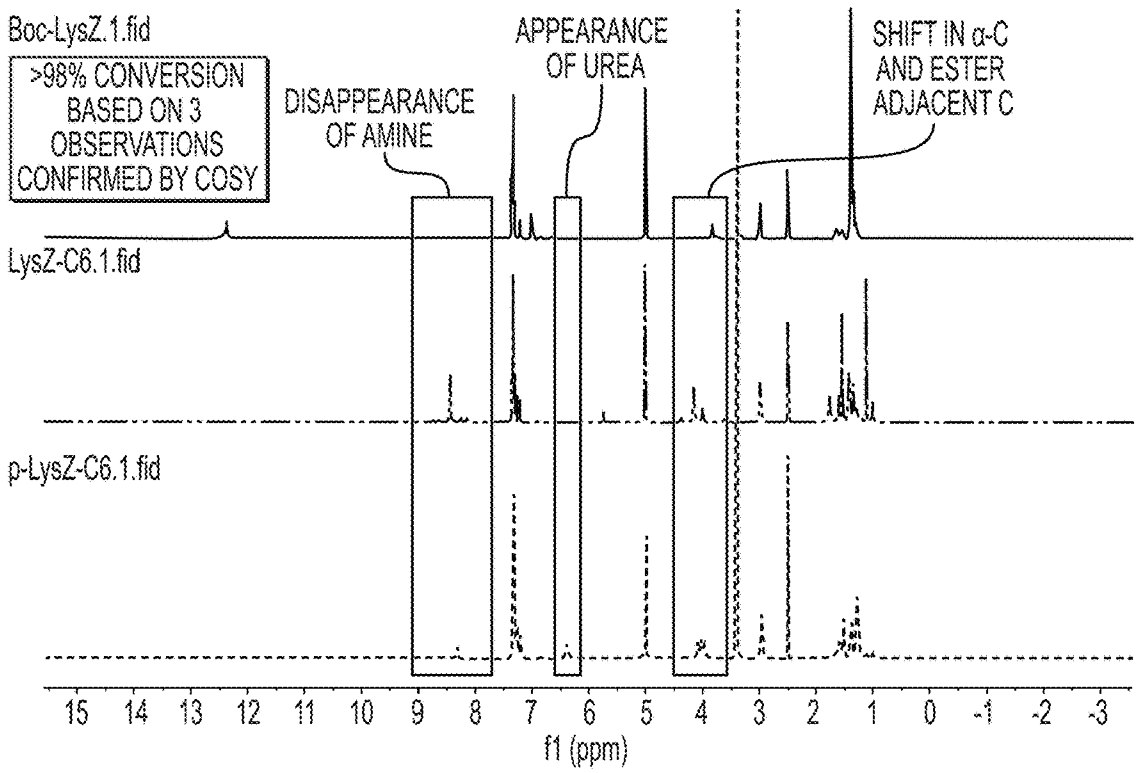

Incorporation of charged amino acids into the PEUs enables electrostatic complexation with drugs/protein cargo of interest. The synthesis of PEUs containing lysine and aspartic acid was confirmed by $^{1}$H NMR and $^{1}$H-$^{1}$H COSY NMR. The structure, $^{1}$H NMR, and $^{1}$H-$^{1}$H COSY NMR of poly(1,6-hexanediol-l-lysine (CBZ))-based PEU (Lys(Z)-C6-PEU) is provided in FIGS. 1-3. Integrations of non-labile hydrogens match well with predicted values for the polymer. COSY confirmed peak assignments based on the presence of expected interactions. Additionally, comparison of the polymer to the monomer and the amino acid confirms a >98% conversion based on the disappearance of the amine peak and appearance of the urea peak after polymerization and the confirmed shift in the peak for the α-C hydrogen and the ester adjacent hydrogens after polymerization.

Figure 4:
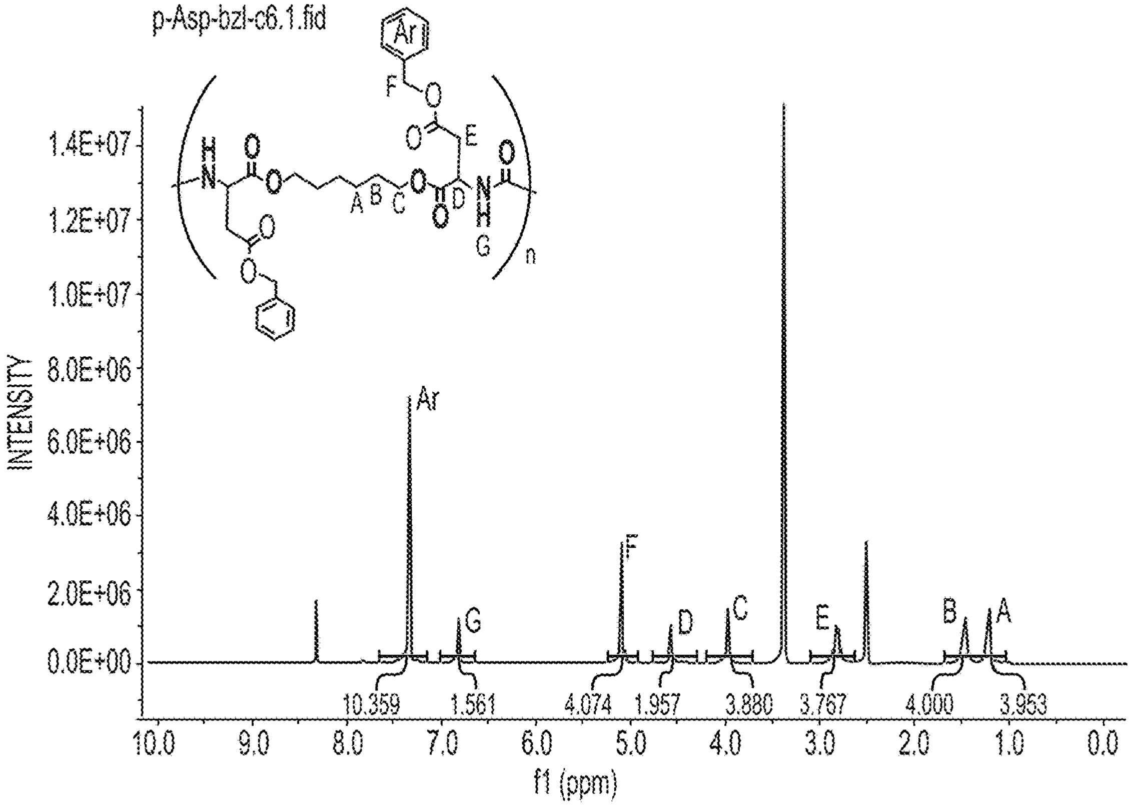
FIGS. 4-6 provide $^1$H NMR, and $^1$H-$^1$H COSY NMR of poly(1,6-hexanediol-l-aspartic acid (OBzl))-based PEU (Asp(OBzl)-C6-PEU).
Figure 5:
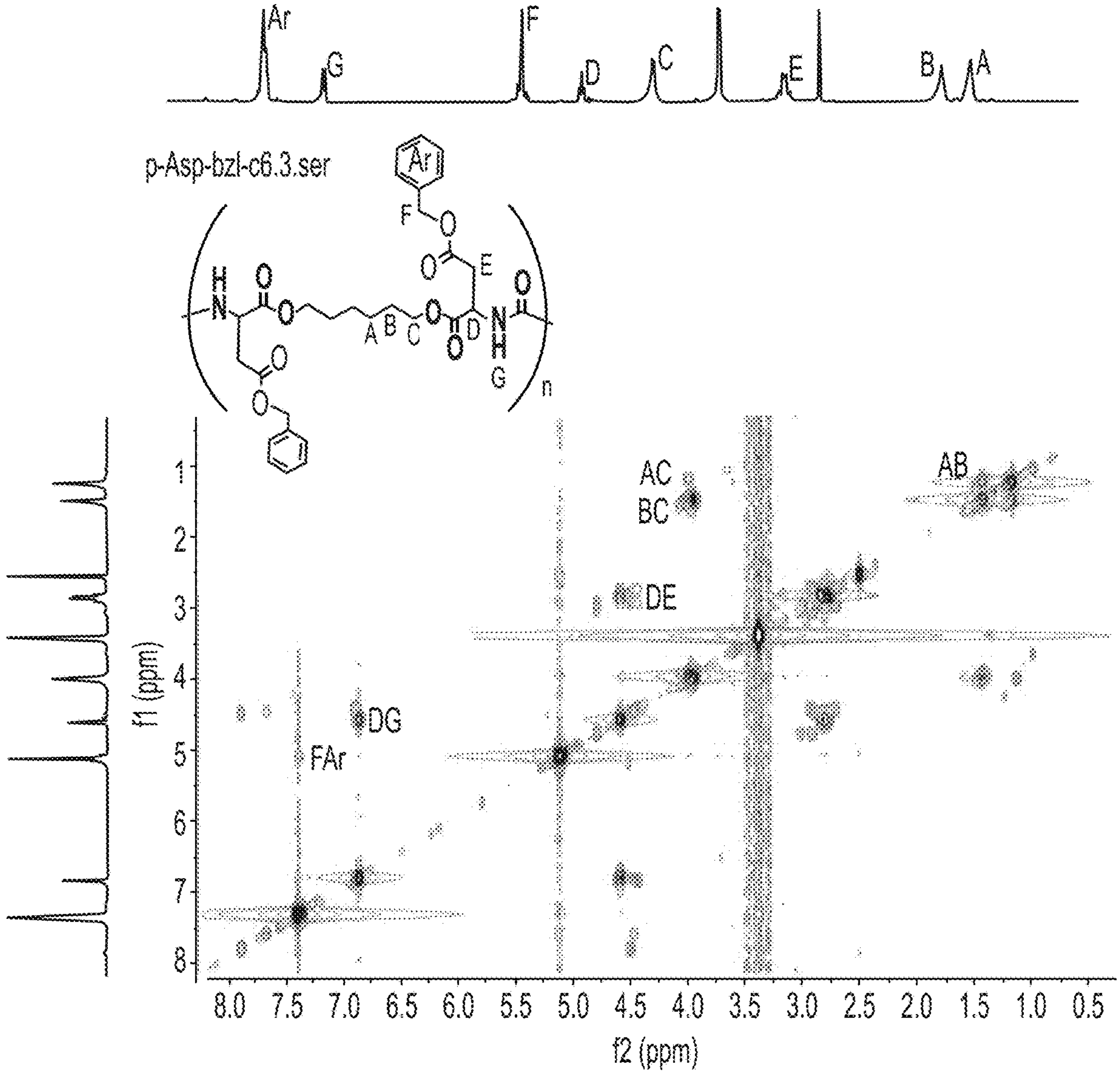
Figure 6:
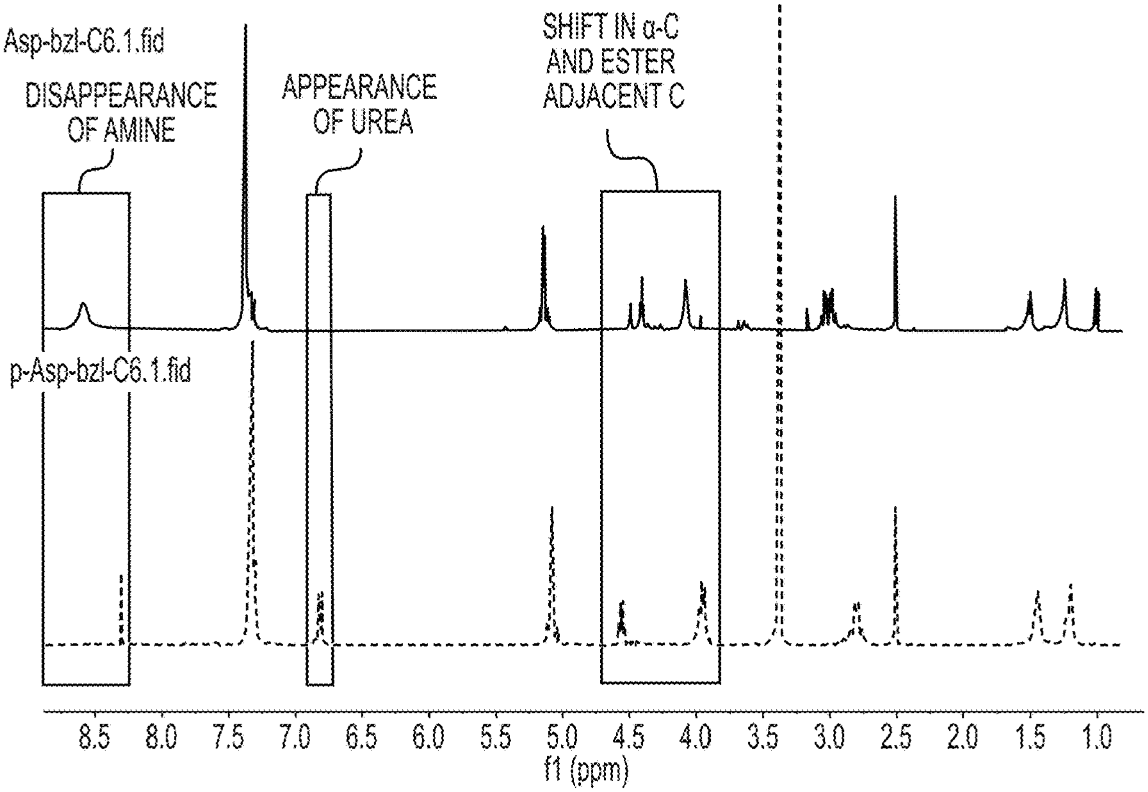

The structure, $^{1}$H NMR, and $^{1}$H-$^{1}$H COSY NMR of poly(1,6-hexanediol-l-aspartic acid (OBzl))-based PEU (Asp(OBzl)-C6-PEU) is provided in FIGS. 4-6. Integrations of non-labile hydrogens match well with predicted values for the polymer. COSY confirmed peak assignments based on the presence of expected interactions. Additionally, comparison of the polymer to the monomer and the amino acid confirms a >98% conversion based on the disappearance of the amine peak and appearance of the urea peak after polymerization and the confirmed shift in the peak for the α-C hydrogen and the ester adjacent hydrogens after polymerization.

Figure 7:
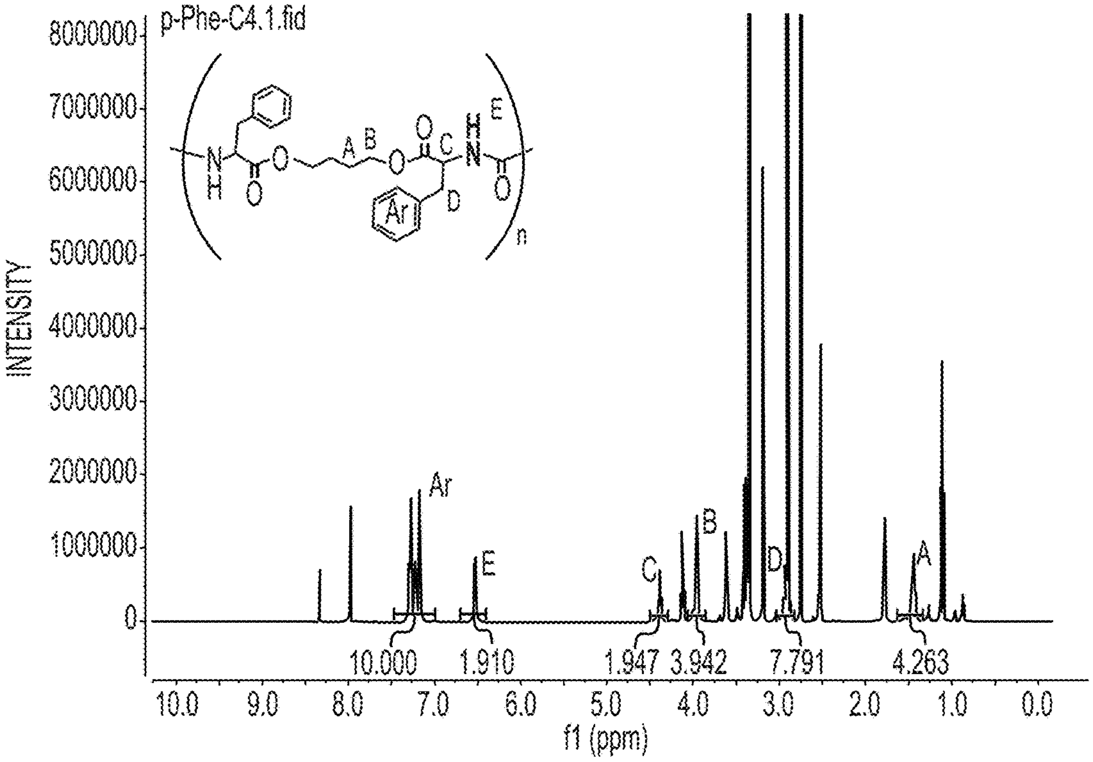
FIGS. 7-9 provide $^1$H NMR, and $^1$H-$^1$H COSY NMR of poly(1,4-butanediol-l-phenylalanine)-based PEU (Phe-C4-PEU).
Figure 8:
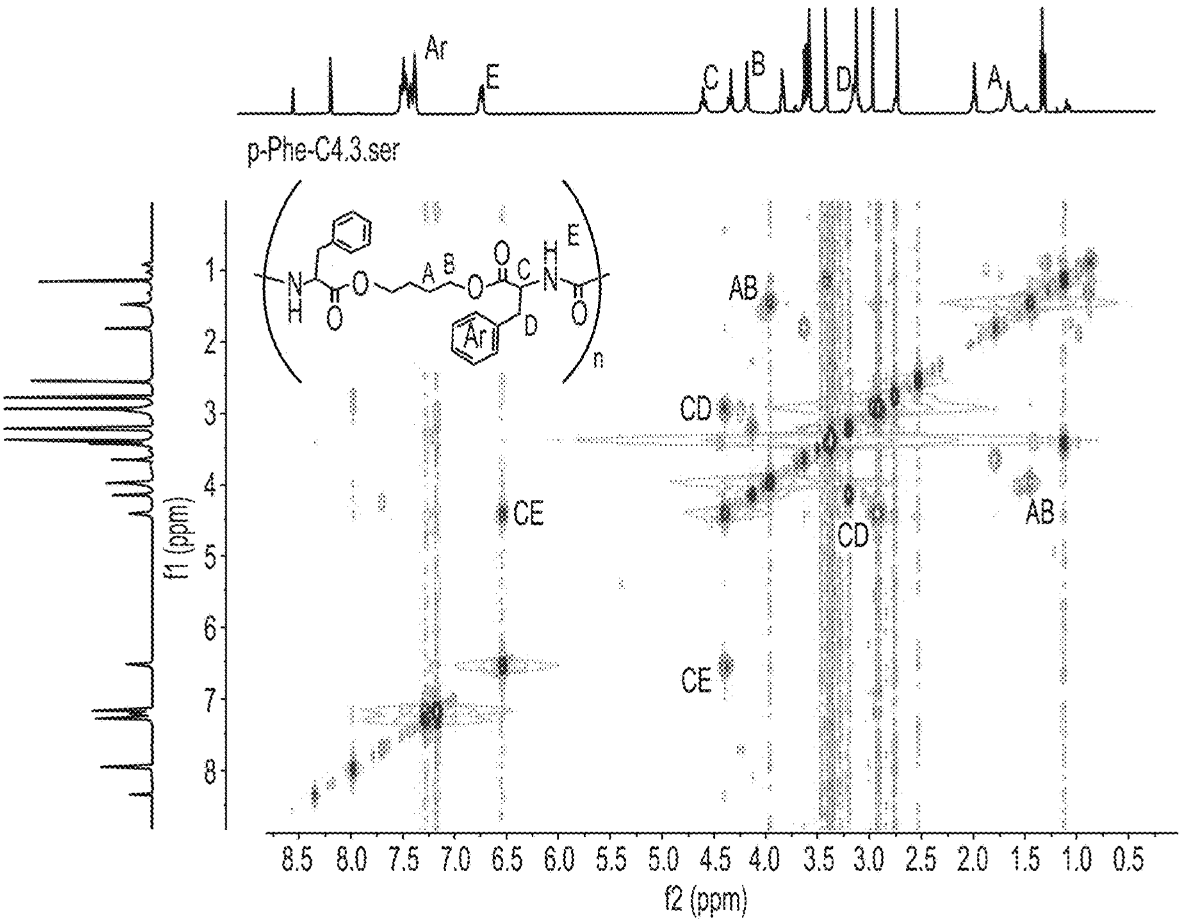
Figure 9:
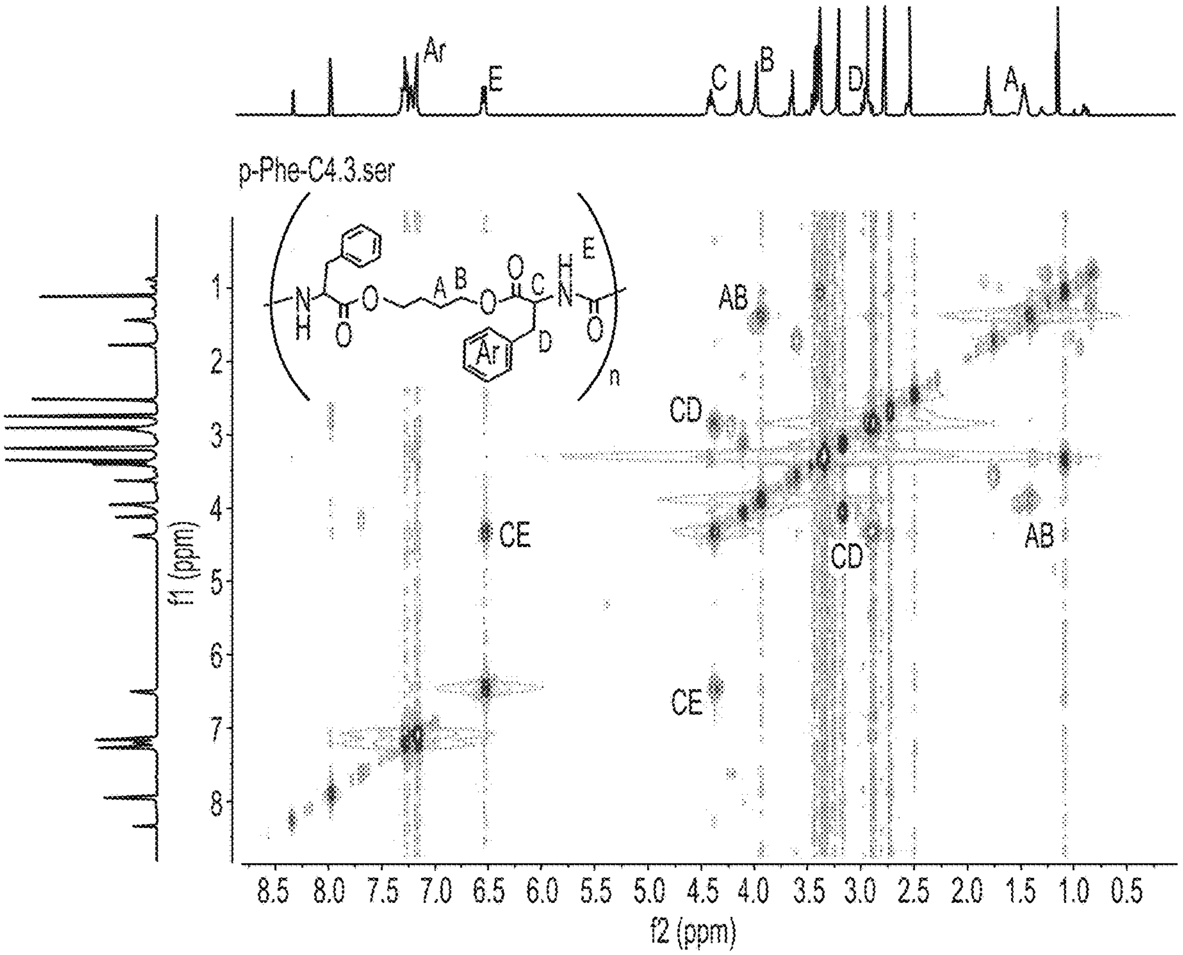

To boost the water solubility of the PEUs, butanediol (C4), diethylene glycol (DEG), triethylene glycol (TEG), and methyl diethanolamine (MDEA) were incorporated into the PEUs in place of the normally aliphatic diols. Additionally, DEG and TEG may further increase the biocompatibility of these materials. The synthesis of these polymers was also confirmed by $^{1}$H NMR and $^{1}$H-$^{1}$H COSY NMR. The structure, $^{1}$H NMR, and $^{1}$H-$^{1}$H COSY NMR of poly(1,4-butanediol-1-phenylalanine)-based PEU (Phe-C4-PEU) is provided in FIGS. 7-9. Integrations of non-labile hydrogens match well with predicted values for the polymer, except peak D due to residual solvent (DMF). COSY confirmed peak assignments based on the presence of expected interactions. Additionally, comparison of the polymer to the monomer and the amino acid confirms a >98% conversion based on the disappearance of the amine peak and appearance of the urea peak after polymerization and the confirmed shift in the peak for the α-C hydrogen and the ester adjacent hydrogens after polymerization.

Figure 10:
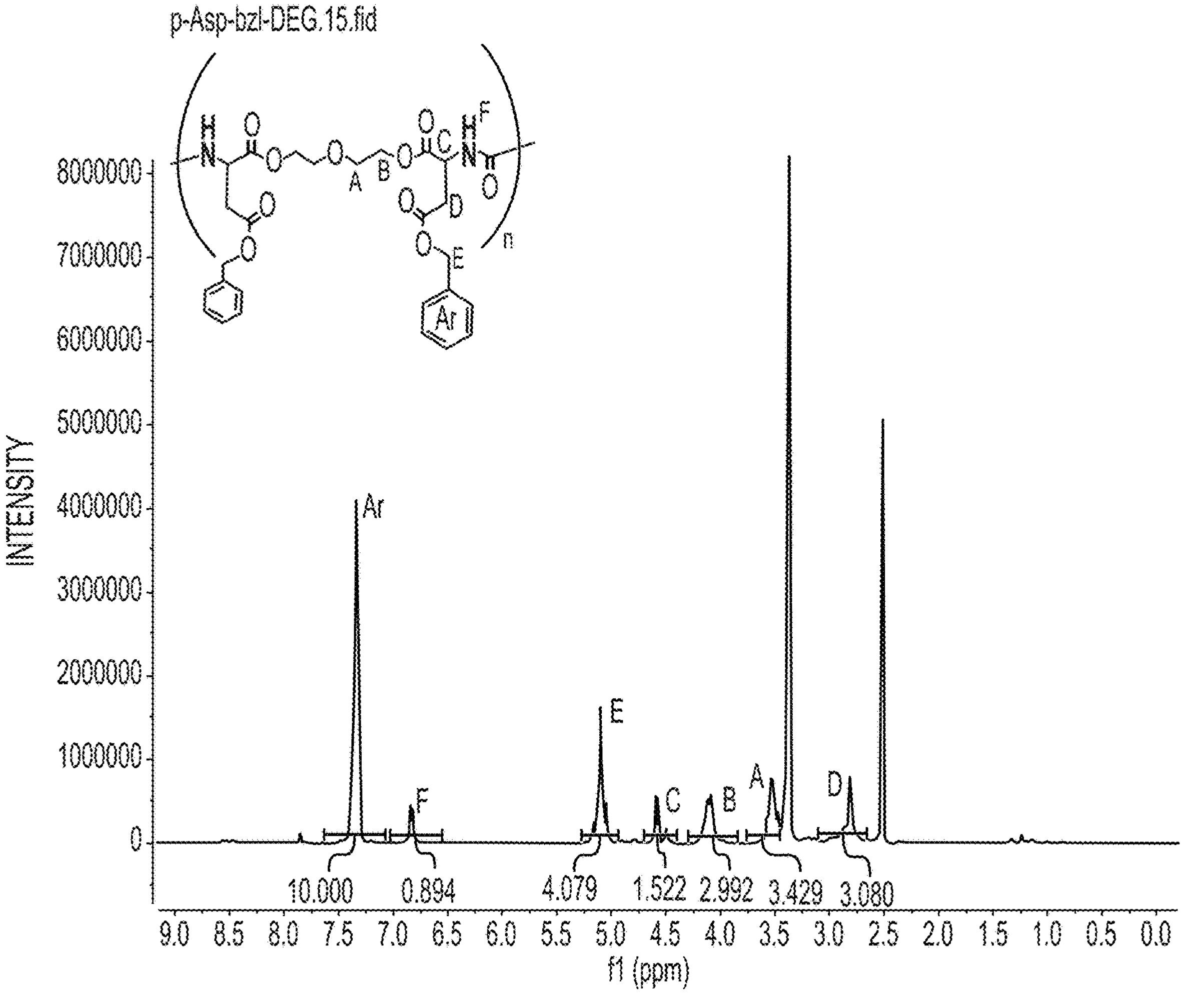
FIGS. 10-12 provide $^1$H NMR, and $^1$H-$^1$H COSY NMR of poly(DEG-l-aspartic acid (OBzl))-based PEU (Asp (OBzl)-DEG-PEU).
Figure 11:
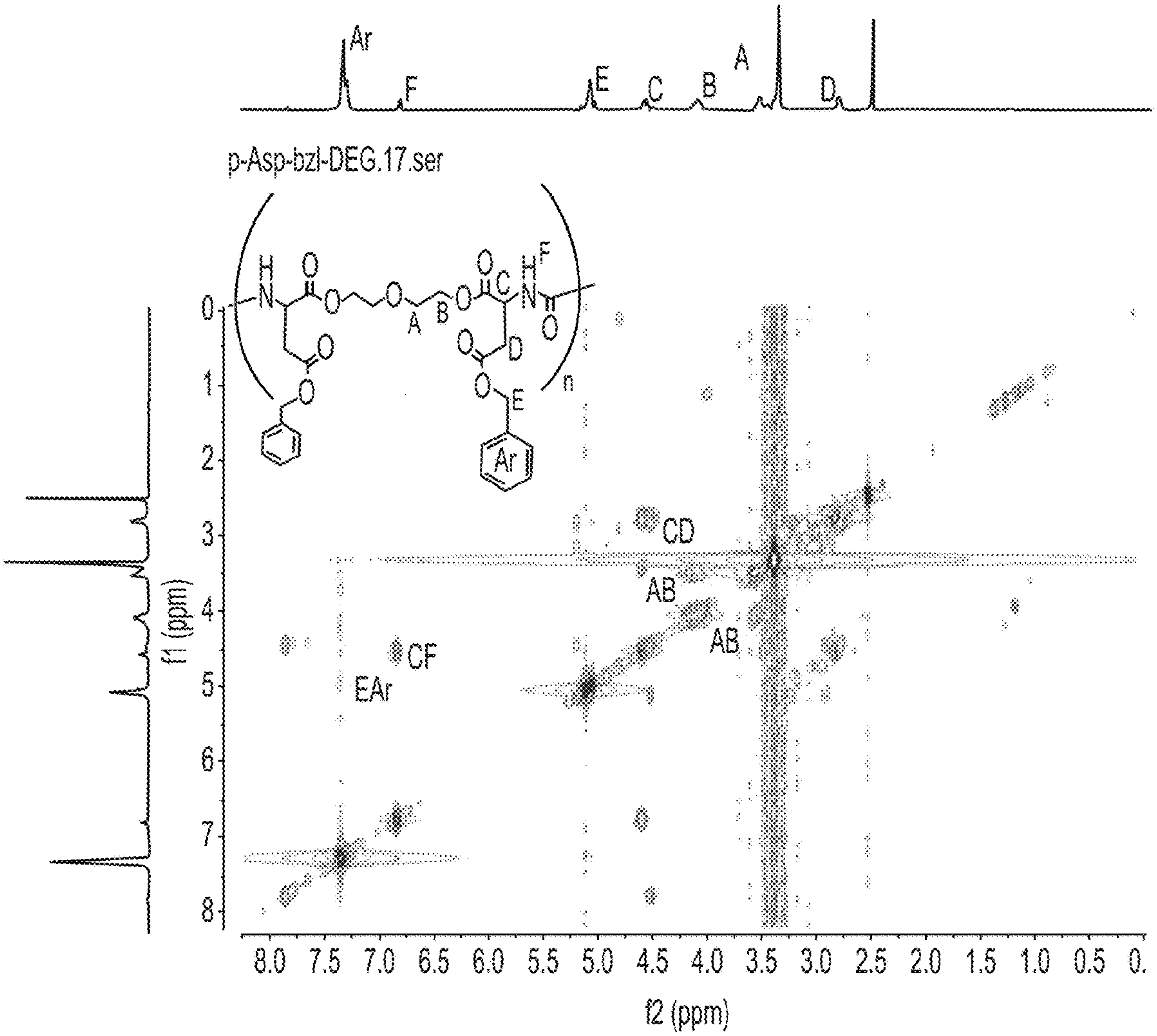
Figure 12:
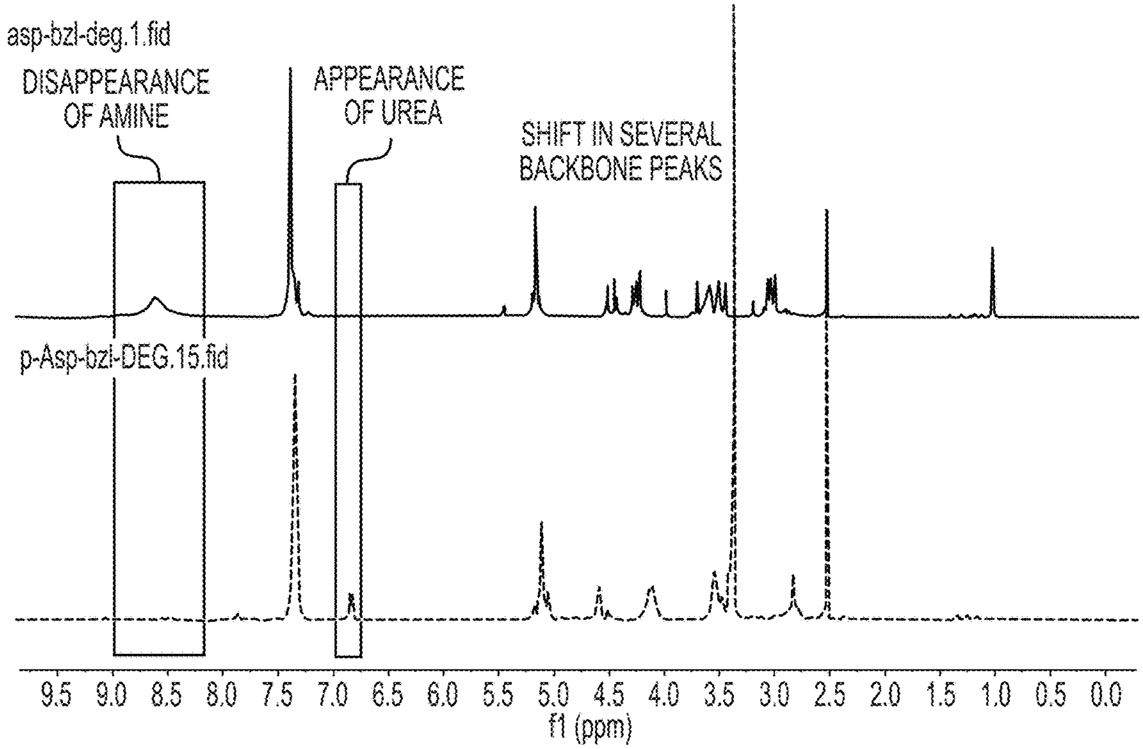

The structure, $^{1}$H NMR, and $^{1}$H-$^{1}$H COSY NMR of poly(DEG-l-aspartic acid (OBzl))-based PEU (Asp(OBzl)-DEG-PEU) is provided in FIGS. 10-12. COSY confirmed peak assignments based on the presence of expected interactions. Additionally, comparison of the polymer to the monomer and the amino acid confirms a >98% conversion based on the disappearance of the amine peak and appearance of the urea peak after polymerization and the confirmed shift in the peak for the α-C hydrogen and the ester adjacent hydrogens after polymerization.

Figure 13:
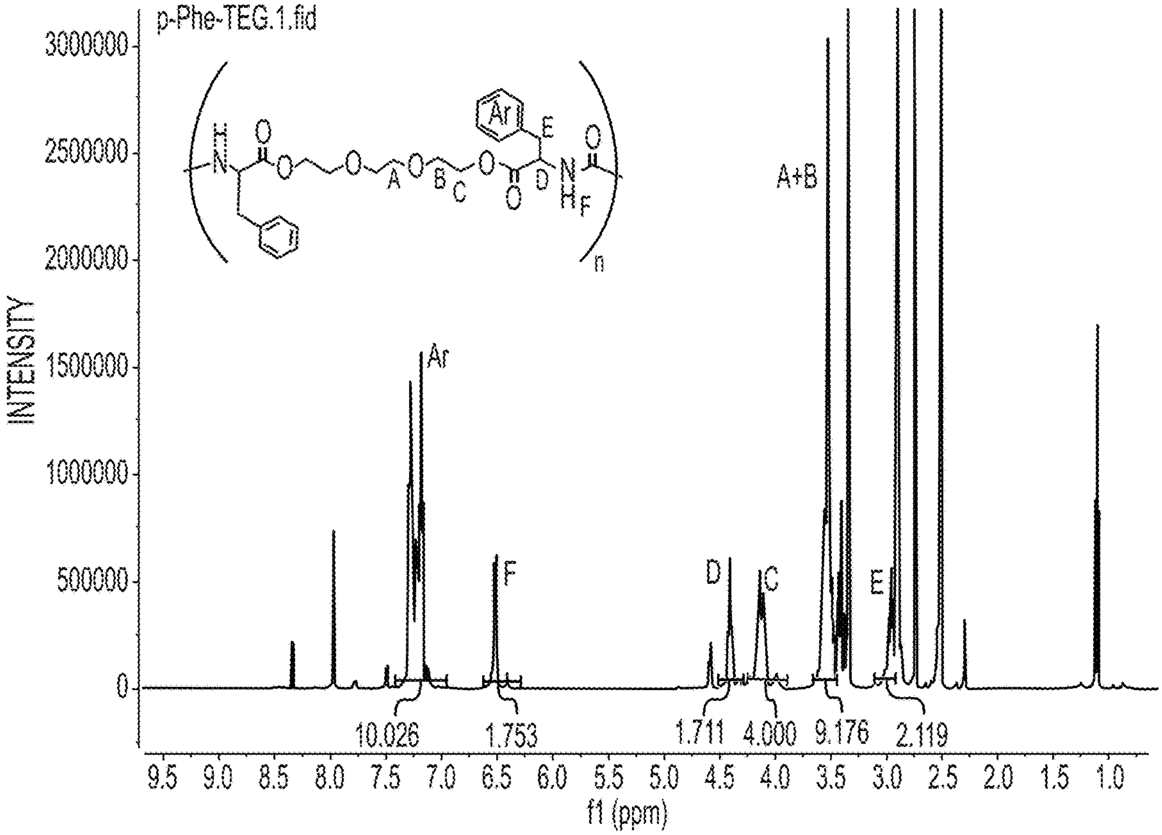
FIGS. 13-15 provide $^1$H NMR, and $^1$H-$^1$H COSY NMR of poly(TEG-l-phenylalanine)-based PEU (Phe-TEG-PEU).
Figure 14:
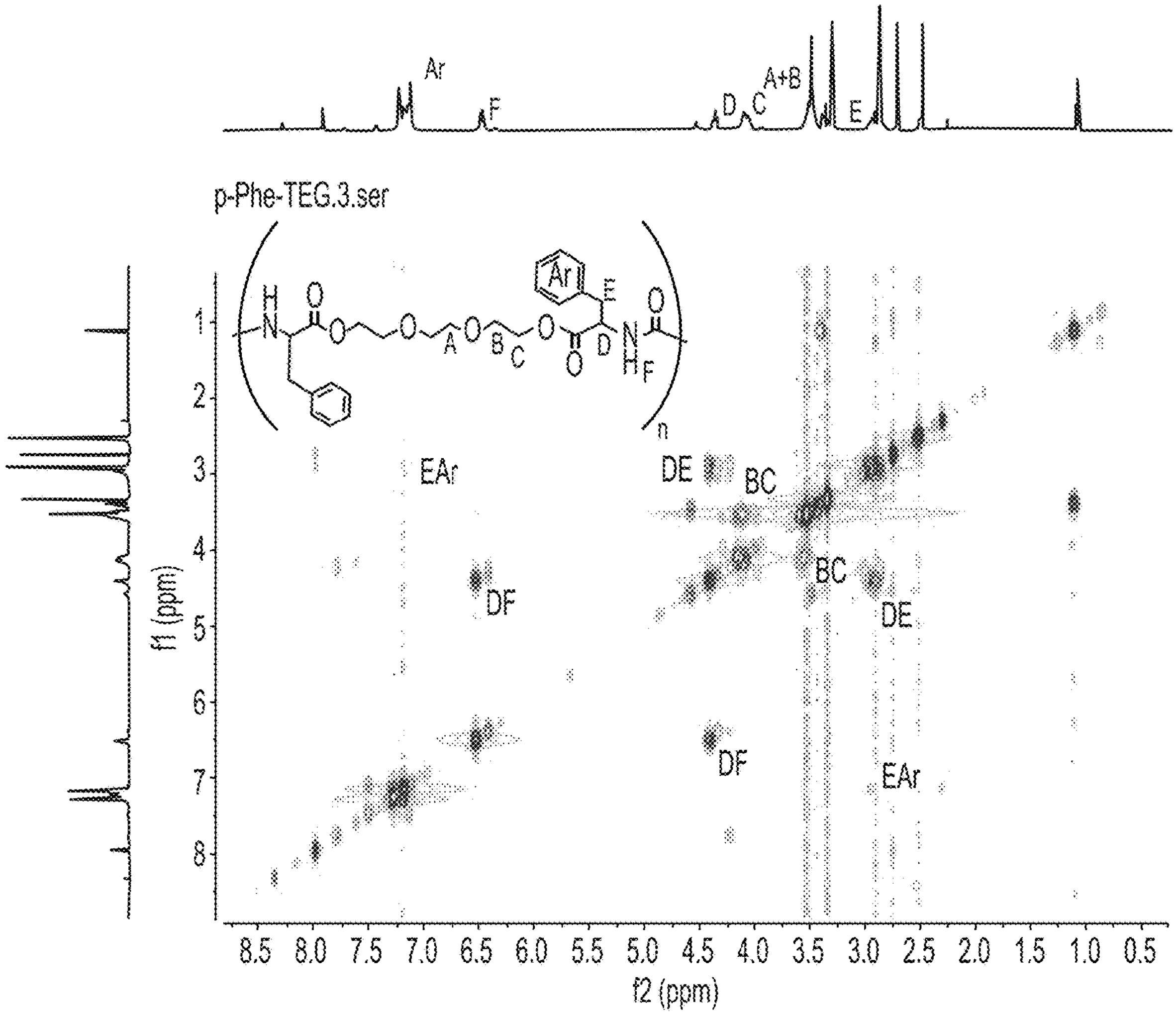
Figure 15:
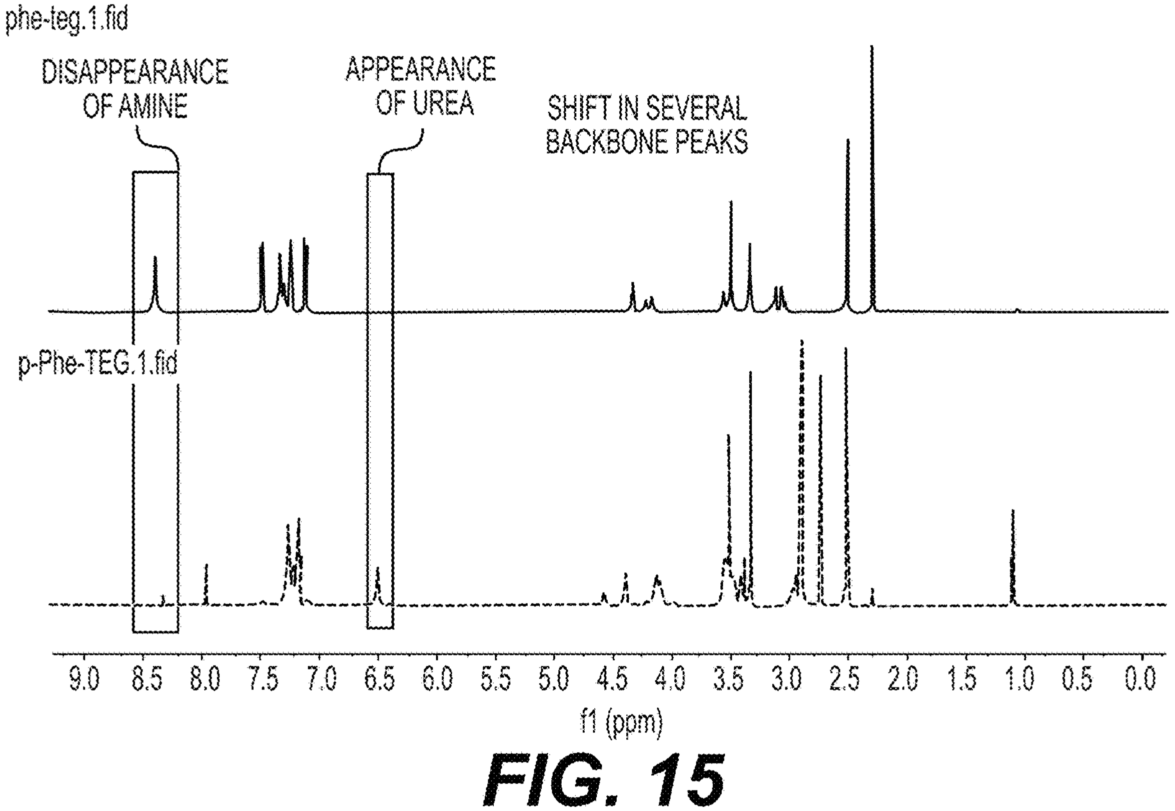

The structure, $^{1}$H NMR, and $^{1}$H-$^{1}$H COSY NMR of poly(TEG-l-phenylalanine)-based PEU (Phe-TEG-PEU) is provided in FIGS. 13-15. Integrations of non-labile hydrogens match well with predicted values for the polymer except the combined A+B peak and the E peak due to solvent interference. COSY confirmed peak assignments based on the presence of expected interactions. Additionally, comparison of the polymer to the monomer and the amino acid confirms a >98% conversion based on the disappearance of the amine peak and appearance of the urea peak after polymerization and the confirmed shift in the peak for the α-C hydrogen and the ester adjacent hydrogens after polymerization.

Figure 16:
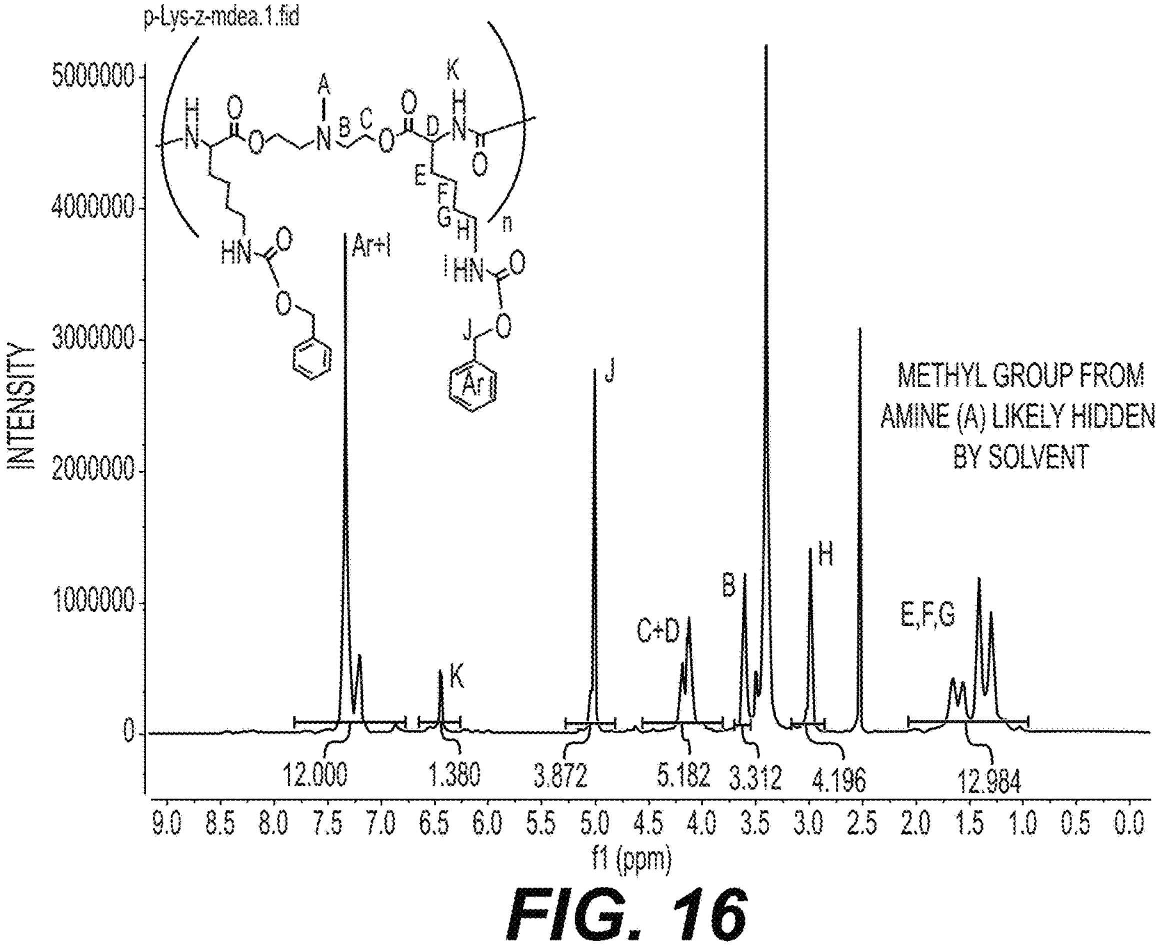
FIGS. 16-18 provide $^1$H NMR, and $^1$H-$^1$H COSY NMR of poly(MDEA-l-lysine (CBZ))-based PEU (Lys(Z)-MDEA-PEU).
Figure 17:
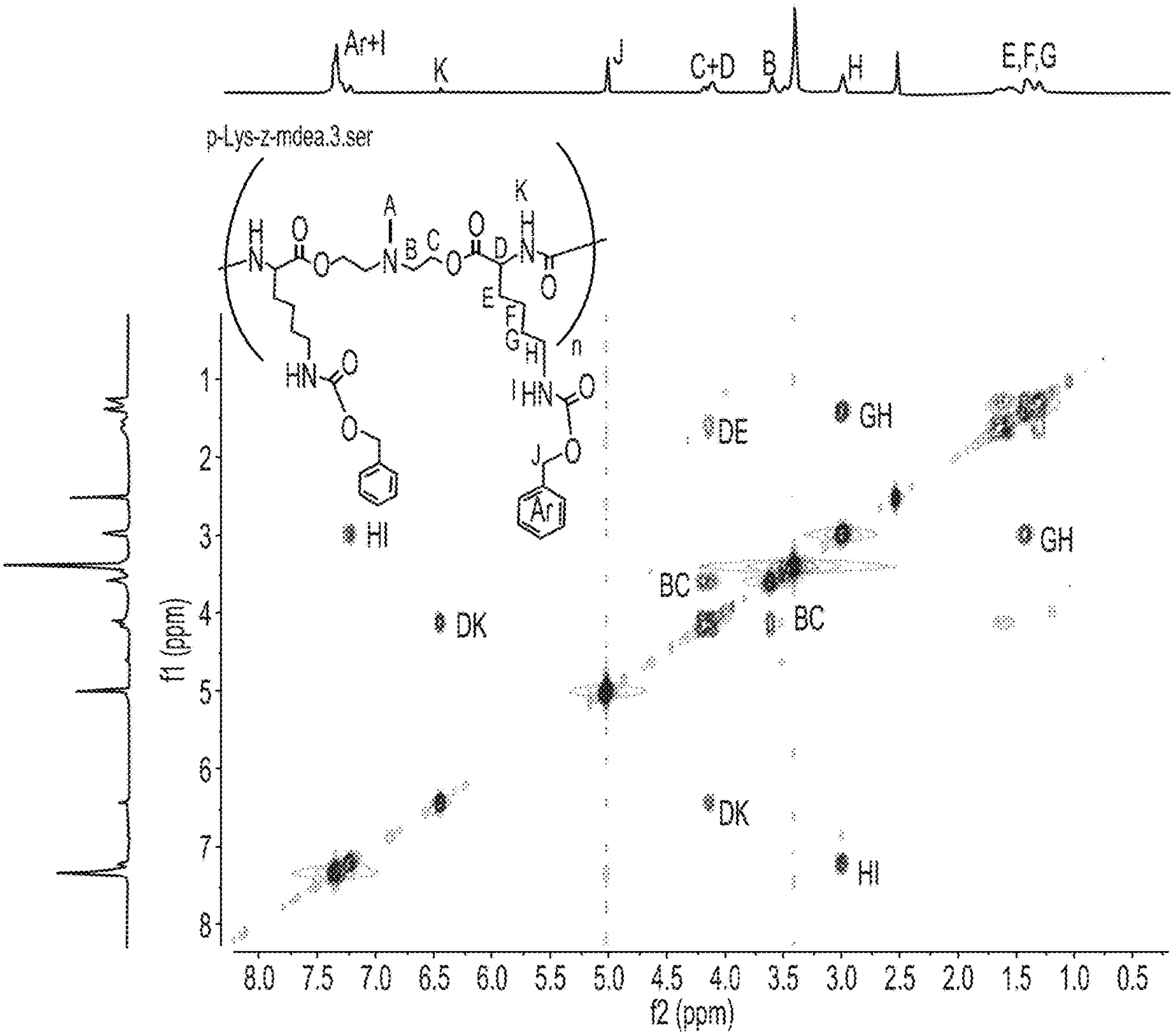
Figure 18:
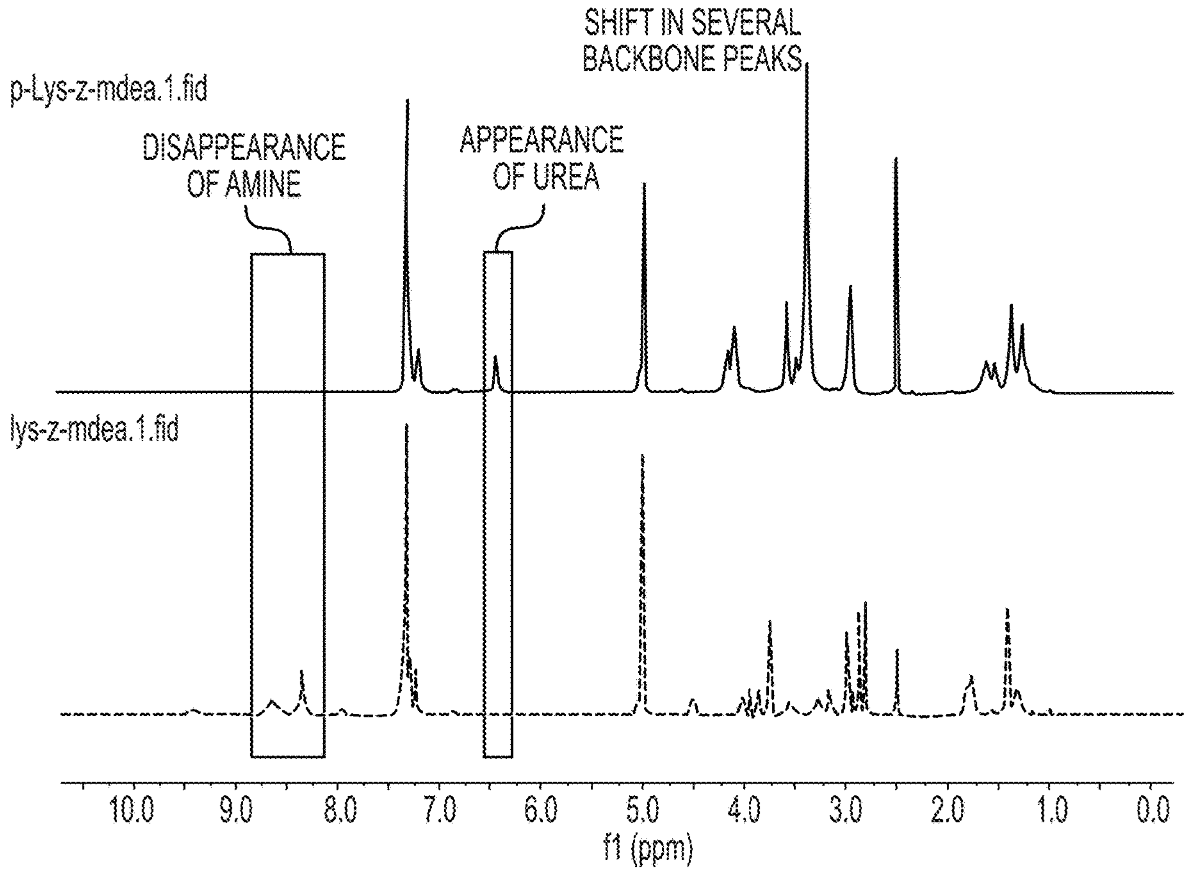

The structure, $^{1}H$ NMR, and $^{1}H$-$^{1}H$ COSY NMR of poly(MDEA-l-lysine (CBZ))-based PEU (Lys(Z)-MDEA-PEU) is provided in FIGS. 16-18. Integrations of non-labile hydrogens match well with predicted values for the polymer except the A peak which is likely hidden behind the residual DMSO peak. COSY confirmed peak assignments based on the presence of expected interactions. Additionally, comparison of the polymer to the monomer and the amino acid confirms a >98% conversion based on the disappearance of the amine peak and appearance of the urea peak after polymerization and the confirmed shift in the peak for the α-C hydrogen and the ester adjacent hydrogens after polymerization.

In summary, synthetic chemistries for both diol midblock and the amino acid constituents of PEUs have been demonstrated to be incorporated in PEUs. These chemistries will enable an expansion of the applications to which this class of materials can be applied, including drug delivery.

Those skilled in the art will recognize, or be able to ascertain using no more than routine experimentation, many equivalents to the specific embodiments of the invention described herein. Such equivalents are intended to be encompassed by the following claims.

We claim:

1. A poly(ester urea) comprising two or more units having a structure:

$[(AA1)_p\text{-linker-}(AA2)_q]$  Formula I wherein:

at least two units are covalently bonded via a urea bond;

each of AA1 and AA2 is independently an unprotected or protected amino acid monomer;

p and q are independently 1 or 2; and wherein the linker is a branched chemical moiety consisting of a structure selected from:

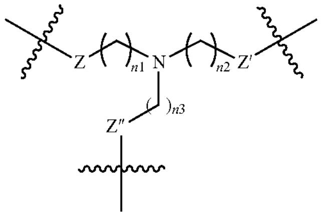
,

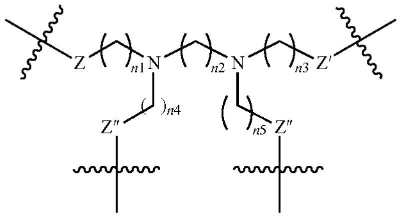
,

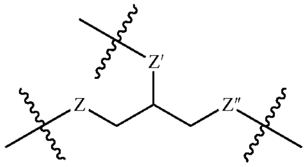
,

-continued

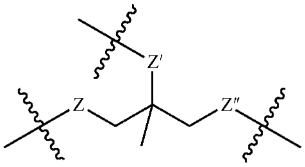
,

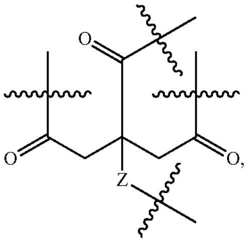
,

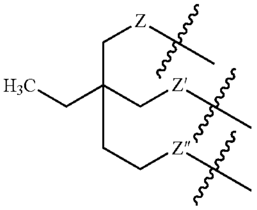
,

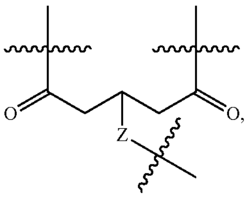
,

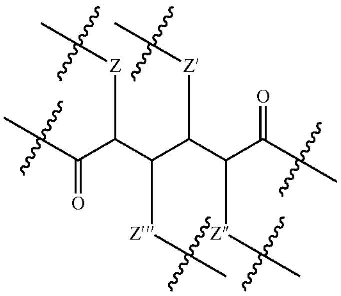
,

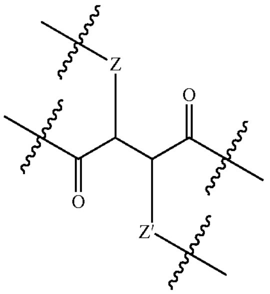
,

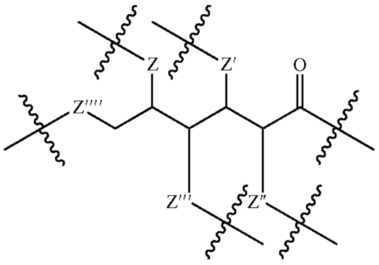
,

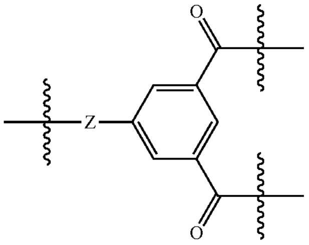
,

-continued

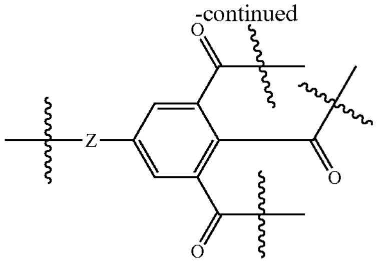

,

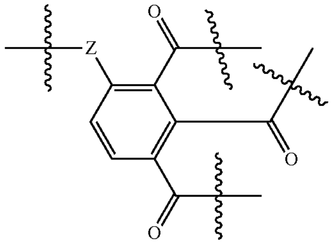

, and a combination thereof, wherein each Z, Z', Z'', Z''', and Z'''' is independently O, S, or NRy, wherein Ry is hydrogen, substituted or unsubstituted alkyl, substituted or unsubstituted aryl, and each n1, n2, n3, n4, and n5 is independently an integer between 1 and 20.

2. The poly(ester urea) of claim 1, comprising a structure:

$[(AA1)\text{-linker-}(AA2)]_n$ Formula II wherein n is an integer greater than 2 and less than 1000.

3. The poly(ester urea) of claim 1, wherein the amino acid monomers comprise a cationic amino acid monomer, an anionic amino acid monomer, an aromatic amino acid monomer, or a side chain protected derivative thereof.

4. The poly(ester urea) of claim 1, wherein the amino acid monomers comprise a cationic amino acid monomer, an anionic amino acid monomer, or a side chain protected derivative thereof.

5. The poly(ester urea) of claim 1, wherein the amino acid monomers comprise a cationic amino acid monomer or a side chain protected derivative thereof.

6. The poly(ester urea) of claim 1, wherein the amino acid monomers comprise an anionic amino acid monomer or a side chain protected derivative thereof.

7. The poly(ester urea) of claim 1, wherein the amino acid monomers comprise an aromatic amino acid monomer or a side chain protected derivative thereof.

8. The poly(ester urea) of claim 1, wherein the amino acid monomers are selected from lysine, arginine, ornithine, histidine, aspartic acid, glutamic acid, phenylalanine, tyrosine, or a side chain protected derivative thereof.

9. The poly(ester urea) of claim 3, wherein the side chain protected derivative contains a protecting moiety selected from benzyloxycarbonyl, benzyl, allyloxycarbonyl, 9-fluorenylmethoxycarbonyl, tert-butyloxycarbonyl, tert-butyl, trityl, 2,4-dimethoxybenzyl, 9-fluorenylmethyl, 2,2,4,6,7-pentamethyl-2,3-dihydrobenzofuran-5-sulfonyl, 9-xanthenyl, tosyl, benzyloxymethyl, formyl, tert-butyldimethylsilyl, allyl, o-nitrobenzyl, acetamidomethyl.

10. The poly(ester urea) of claim 3, wherein the side chain protected derivative contains a protecting moiety selected from benzyloxycarbonyl or benzyl.

11. The poly(ester urea) of claim 1, wherein the linker is a branched chemical moiety consisting of a structure selected from:

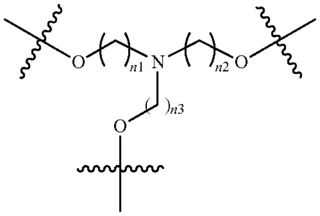

,

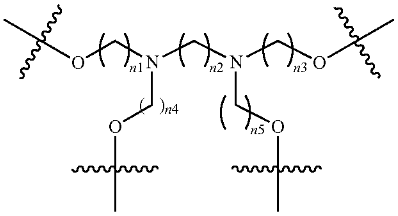

,

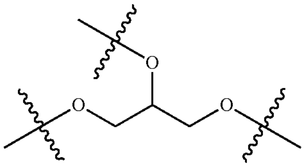

,

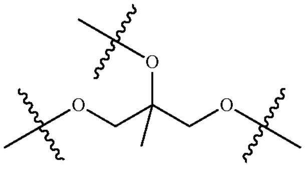

,

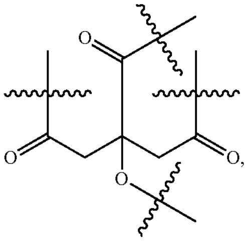

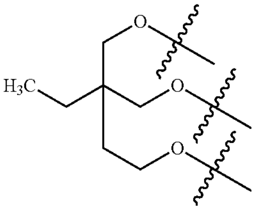

,

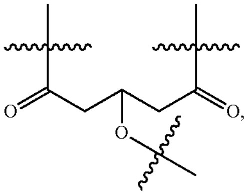

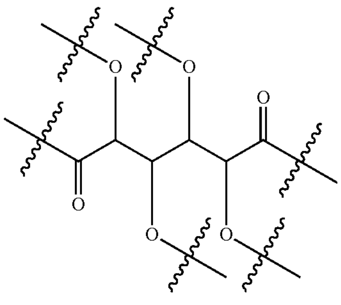

,

-continued

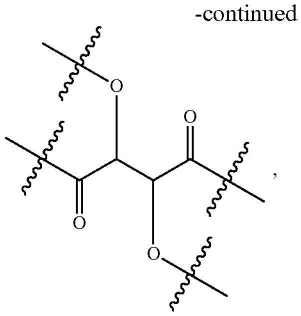

,

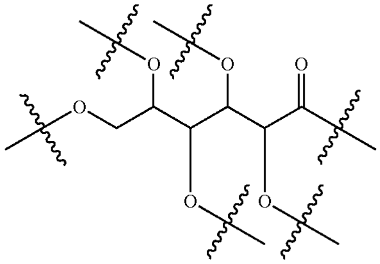

,

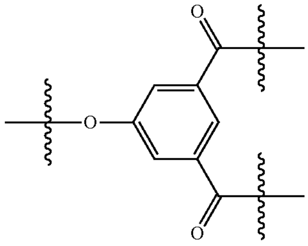

,

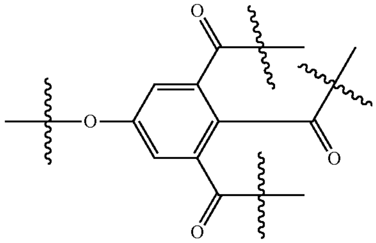

,

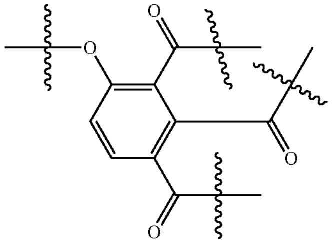

, and a combination thereof, wherein n1, n2, n3, n4, and n5 are 2.

12. A polyplex comprising the poly(ester urea) of claim 1 and one or more therapeutic, prophylactic, or diagnostic agents.

13. The polyplex of claim 12, comprising a polyelectrolyte complex of the poly(ester urea) and the one or more therapeutic, prophylactic, or diagnostic agents.

14. The polyplex of claim 12, in the form of a micelle, a liquid polyplex, or a thin-film coating.

15. A pharmaceutical composition comprising the polyplex of claim 12 and a pharmaceutically acceptable carrier.

16. A method of administering one or more therapeutic, prophylactic, or diagnostic agents to a subject in need thereof, the method comprising injecting or transplanting the polyplex of claim 12 to the subject.

17. A poly(ester urea), having a structure selected from:

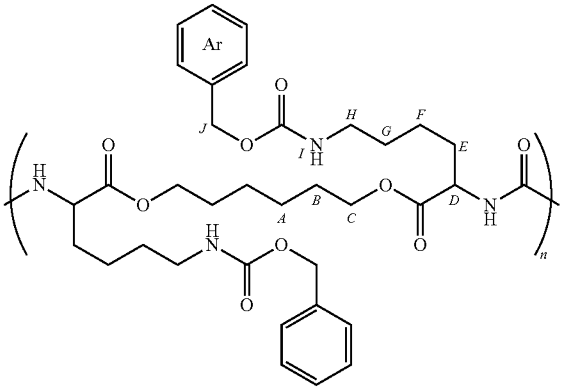

,

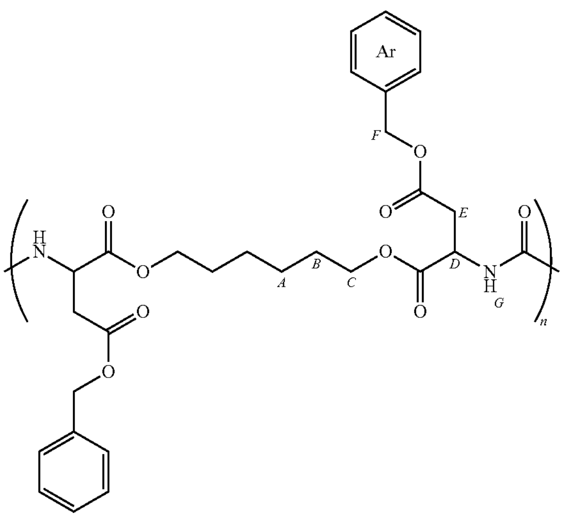

,

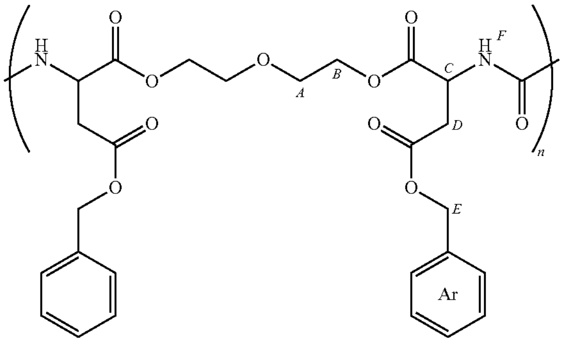

,

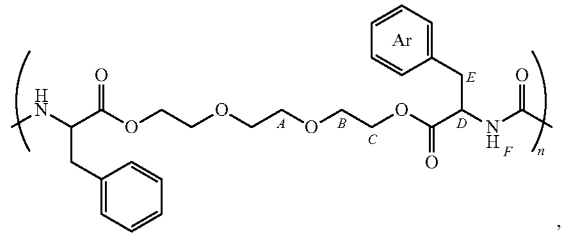

,

-continued
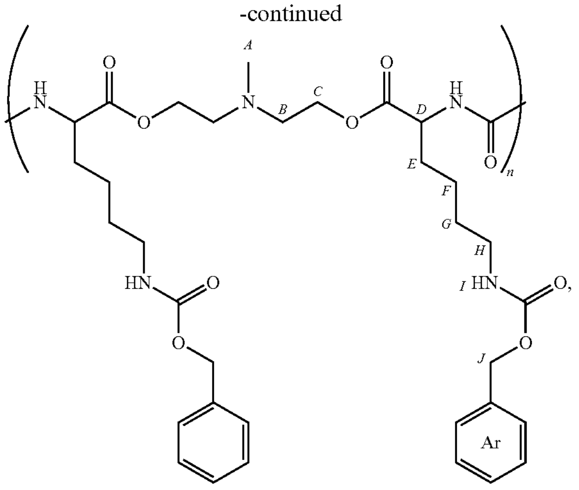
and combinations thereof,
wherein n is greater than 2 and less than 1000
wherein each of the poly(ester urea) has at least two structures recited above covalently bonded via a urea bond.
* * * * *